US007813798B2

(12) United States Patent
Bornzin et al.

(10) Patent No.: US 7,813,798 B2
(45) Date of Patent: Oct. 12, 2010

(54) SYSTEMS AND METHODS FOR PREVENTING, DETECTING, AND TERMINATING PACEMAKER MEDIATED TACHYCARDIA IN BIVENTRICULAR IMPLANTABLE CARDIAC STIMULATION SYSTEMS

(75) Inventors: Gene A. Bornzin, Simi Valley, CA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 774 days.

(21) Appl. No.: 11/734,130

(22) Filed: Apr. 11, 2007

(65) Prior Publication Data

US 2007/0244521 A1    Oct. 18, 2007

Related U.S. Application Data

(63) Continuation of application No. 10/367,325, filed on Feb. 13, 2003, now abandoned.

(60) Provisional application No. 60/357,437, filed on Feb. 14, 2002.

(51) Int. Cl.
*A61N 1/362* (2006.01)
(52) U.S. Cl. .......................................... 607/9
(58) Field of Classification Search ................ 607/9
See application file for complete search history.

(56) References Cited

U.S. PATENT DOCUMENTS

| 4,569,350 | A |   | 2/1986  | Mumford et al. |
|-----------|---|---|---------|----------------|
| 4,928,688 | A |   | 5/1990  | Mower          |
| 5,074,308 | A |   | 12/1991 | Sholder et al. |
| 5,085,215 | A | * | 2/1992  | Nappholz et al. ............ 607/17 |
| 5,167,224 | A |   | 12/1992 | Limousin et al.|
| 5,496,350 | A |   | 3/1996  | Lu             |
| 5,685,315 | A |   | 11/1997 | McClure et al. |
| 5,779,645 | A |   | 7/1998  | Olson et al.   |
| 5,782,887 | A |   | 7/1998  | van Krieken et al. |
| 5,810,739 | A |   | 9/1998  | Bornzin et al. |
| 5,978,708 | A |   | 11/1999 | Bonnet et al.  |
| 6,169,918 | B1|   | 1/2001  | Haefner et al. |
| 6,238,420 | B1|   | 5/2001  | Bakels et al.  |
| 6,240,313 | B1|   | 5/2001  | Esler          |
| 6,285,907 | B1|   | 9/2001  | Kramer et al.  |
| 6,480,739 | B1|   | 11/2002 | Nigam et al.   |

(Continued)

OTHER PUBLICATIONS

Barold, S.S. et al, "Cross-Ventilation Endless Loop Tachycardia During Biventricular Pacing" PACE 2001;24:1821-1823.

(Continued)

*Primary Examiner*—Carl H Layno
*Assistant Examiner*—Jeremiah T Kimball

(57) ABSTRACT

Various techniques are described for preventing pacemaker mediated tachycardia (PMT) within biventricular pacing systems and for detecting and terminating PMT should it nevertheless arise. In a first prevention technique, refractory periods applied to the atrial channel are synchronized to begin with a second of a pair of ventricular pacing pulses to more effectively prevent T-wave oversensing on the atrial channel. In a second prevention technique, the sensitivity of the atrial channel is reduced during T-waves also to prevent T-wave oversensing. In a third prevention technique, template matching is performed on the ventricular channels to prevent T-wave oversensing. In a fourth prevention technique, T-wave detection windows are applied to both the ventricular and atrial channels subsequent to any paced or sensed events.

24 Claims, 14 Drawing Sheets

U.S. PATENT DOCUMENTS

| | | | |
|---|---|---|---|
| 6,516,225 | B1 | 2/2003 | Florio |
| 6,609,028 | B2 * | 8/2003 | Struble ........................ 607/14 |
| 6,625,491 | B2 | 9/2003 | Ripart |
| 2001/0005790 | A1 | 6/2001 | Ripart |
| 2001/0016693 | A1 | 8/2001 | Bonnet et al. |
| 2002/0082653 | A1 | 6/2002 | Stahmann et al. |
| 2002/0183792 | A1 | 12/2002 | Struble |

OTHER PUBLICATIONS

Van Gelder, B.M. et al, "Pacemaker-Mediated Tachycardia in a Biventricular Pacing System" PACE 2001;24:1819-1820.

NonFinal Office Action, mailed Sep. 1, 2005: Related U.S. Appl. No. 10/367,325.

Final Office Action, mailed Feb. 7, 2006: Related U.S. Appl. No. 10/367,325.

NonFinal Office Action, mailed Jun. 1, 2006: Related U.S. Appl. No. 10/367,325.

Final Office Action, mailed Oct. 12, 2006: Related U.S. Appl. No. 10/367,325.

Advisory Office Action, mailed Feb. 13, 2007: Related U.S. Appl. No. 10/367,325.

NonFinal Office Action, mailed Sep. 1, 2005: Related U.S. Appl. No. 10/367,504.

Notice of Allowance, mailed Nov. 17, 2005: Related U.S. Appl. No. 10/367,504.

Barold, S. Serge et al., "Cross-Ventricular Endless Loop Tachycardia During Biventricular Pacing," PACE 2001; 24: 1821-1823.

Van Gelder, B.M et al., "Pacemaker-Medidated Tachycardia in a Biventricular Pacing System," PACE 2001; 24: 1819-1820.

* cited by examiner

SUMMED AND
RECTIFIED
VENTRICULAR
SIGNALS

ATRIAL
EGM

SYSTEMS AND METHODS FOR PREVENTING, DETECTING, AND TERMINATING PACEMAKER MEDIATED TACHYCARDIA IN BIVENTRICULAR IMPLANTABLE CARDIAC STIMULATION SYSTEMS

CROSS-REFERENCE TO RELATED APPLICATIONS

This application is a continuation of U.S. patent application Ser. No. 10/367,325, titled "System and Method for Preventing, Detecting, and Terminating Pacemaker Mediated Tachycardia in Biventricular Implantable Cardiac Stimulation Device," filed Feb. 13, 2003, and which claims the benefit of U.S. Provisional Application No. 60/357,437, filed Feb. 14, 2002.

FIELD OF THE INVENTION

The invention generally relates to implantable cardiac stimulation devices, such as pacemakers or implantable cardioverter/defibrillators ("ICDs") and, in particular, to techniques for preventing pacemaker mediated tachycardia (PMT) within biventricular pacing systems.

BACKGROUND OF THE INVENTION

An arrhythmia is an abnormal heart beat pattern. One example of arrhythmia is bradycardia wherein the heart beats at an abnormally slow rate or wherein significant pauses occur between consecutive beats. Other examples of arrhythmias include tachyarrhythmias wherein the heart beats at an abnormally fast rate. With atrial tachycardia (AT), the atria of the heart beat abnormally fast. With ventricular tachycardia (VT), the ventricles of the heart beat abnormally fast. Though often unpleasant for the patient, a tachycardia is typically not fatal. However, some types of tachycardia, particularly VT, can trigger ventricular fibrillation wherein the heart beats chaotically such that there is little or no net flow of blood from the heart to the brain and other organs. Ventricular fibrillation, if not terminated, is fatal. Hence, it is highly desirable to prevent or terminate arrhythmias, particularly arrhythmias of the type that can lead to a ventricular fibrillation.

For patients prone to arrhythmias, cardiac stimulation devices, such as pacemakers or ICDs can be implanted in the patient to detect the arrhythmias and deliver appropriate electrical therapy to the heart of the patient. Pacemakers typically recognize arrhythmias such as bradycardia and tachycardia and deliver electrical pacing pulses to the heart in an effort to terminate the arrhythmias and cause the heart to revert to a normal sinus rhythm. ICDs additionally recognize atrial fibrillation and ventricular fibrillation and deliver electrical shocks to terminate the fibrillation. To detect the arrhythmias, cardiac stimulation devices carefully monitor characteristics of the heart, particularly the heart rate. The heart rate is tracked by the device by examining electrical signals that result in the contraction and expansion of the chambers of the heart. The contraction of atrial muscle tissue is a result of the atrial depolarization or electrical activation of the atrial tissue manifested as a P-wave in a surface electrocardiogram (ECG). The IEGM is a recording of the electrical signal from within the heart and in the case of the atrium, is referred to as an atrial IEGM. The contraction of ventricular muscle tissue follows the electrical depolarization of the ventricle, which is manifest on the ECG by an R-wave (sometimes referred to as the "QRS complex") and inside the heart as sharp deflection within a ventricular IEGM termed the intrinsic deflection. Recovery of the cardiac electrical potential is manifest as a T-wave on the ECG. With the T-wave, the active cardiac contraction ceases and the ventricle begins to relax and dilate allowing the ventricle to expand and fill with blood in preparation for the next cardiac contraction or heartbeat. A similar phase involving the atrial tissue exists but usually does not result in a detectable signal on the ECG because it is a smaller signal proportional to the P-wave amplitude and both coincides with and is obscured by the QRS complex. The sequence of electrical events that represent P-waves, followed by R-waves (or QRS complexes), followed by T-waves can be detected within IEGM signals sensed using pacing leads implanted inside the heart. Once electrical signals corresponding to P-waves, R-waves, and T-waves are detected within the IEGM signals, an examination of these (and possibly other electrical signals from the heart) is used to detect any arrhythmias.

As noted, the terms P-waves, R-waves and T-waves typically refer to features of the ECG. Herein, however, for the sake of clarity and brevity, the terms will be used more generally to also refer to the corresponding signals as sensed internally. More specifically, the term P-wave will be used to refer to electrical signals representative of the depolarization of the atria regardless of where the signals are sensed. Of course, the particular shape of the P-wave will vary depending upon the sensing locations of the leads and on the particular type of sensing leads (such as unipolar or bipolar). Hence, a P-wave sensed within the left ventricle may differ in shape from a P-wave sensed within the right ventricle. The term R-wave will be used herein to refer to electrical signals representative of the depolarization of the ventricles regardless of where the signals are sensed. Where needed, a distinction will be drawn between left ventricular (LV) R-waves and right ventricular (RV) R-waves. The term LV R-wave refers to electrical signals representative of the depolarization of the left ventricle regardless of where the signals are sensed. The term RV R-wave refers to electrical signals representative of the depolarization of the left ventricle regardless of where the signals are sensed. The term T-wave will be used herein to refer to electrical signals representative of the repolarization of the ventricles as sensed by one or more leads placed within the heart. Again, where needed, a distinction and may be drawn between LV T-waves and RV T-waves. Finally, where an electrical signal is generated in one chamber but sensed in another, it will be referred to, where needed, as a far field signal. Hence, a P-wave sensed in the ventricles is a far field P-wave. An LV R-wave sensed in the right ventricle is a far field LV R-wave.

Once an arrhythmia has been detected, the implantable cardiac simulation device provides the appropriate electrical therapy to the heart, typically using the same leads used to sense the IEGM signals. With single-chambered pacemakers, only a single lead is provided for pacing and sensing at a single location within only one of the chambers of the heart, typically the right ventricle. With dual-chambered pacemakers, two leads are typically provided such that pacing and sensing can be performed in two chambers of the heart, typically the right atrium and right ventricle. With biventricular pacemakers, an additional lead is provided into the left ventricle such that pacing and sensing can be performed in both ventricles. Biventricular pacemakers also usually have a lead mounted in the right atrium as well. Hence, biventricular pacemakers typically receive three sets of electrical signals sensed separately in the right atrium and the left and right ventricles. These electrical signals are processed within the pacemaker on separate channels (a right atrial channel, a left ventricular channel and a right ventricular channel), and signals corresponding to P-waves, R-waves, and T-waves can be identified, depending upon the programming of the implantable device, within the separate channels. Biventricular pacing is particularly advantageous because it permits the timing of contractions of the left and right ventricles to be synchronized as needed to achieve optimal pacing therapy. In particular, biventricular pacemakers have shown the ability to increase the performance of patients with congestive heart failure (CHF) by synchronizing the contraction between the left and right ventricles.

Although cardiac stimulation devices are generally quite effective in detecting and terminating arrhythmias such as tachycardia, in rare cases the stimulation device actually causes tachycardias to occur within the patient, typically as a result of misidentification of P-waves, R-waves, or T-waves. These induced tachycardias are referred to as pacemaker mediated tachycardias. PMTs can arise, for example, within dual-chambered pacemakers because of "retrograde conduction" wherein the depolarization of the ventricles propagates backwards into the atria, causing the atria to depolarize prematurely. As noted, atrial depolarization is manifest by the occurrence of a P-wave, frequently referred to in this particular context as a "retrograde P-wave". A retrograde P-wave appears within an IEGM substantially the same as a natural P-wave except that it occurs much too soon after a ventricular contraction. (A "natural" P-wave results from the natural AV synchrony of the heart as set by the heart's natural sinus rhythm, and is hereafter referred to as a "sinus" P-wave.) Various techniques have been provided for detecting and preventing PMTs that arise from retrograde conduction with dual chambered pacemakers. One particularly effective technique is described in the U.S. Pat. No. 5,074,308 to Sholder et al., entitled "System and Method for Recognizing Pacemaker-Mediated Tachycardia".

PMTs are particularly problematic within biventricular pacemakers because of the risk of the detecting the electrical signals associated with the depolarization of one chamber within other chambers. For example, the electrical depolarization of the right ventricle may be detected within the left ventricular channel and vice versa. Likewise, the electrical depolarization of either the right or left ventricle may be detected on the atrial channel. Hence, there is generally a greater chance of misidentification of electrical signals within biventricular system than in single- or dual-chambered systems and so there is a generally a greater risk of onset of PMT.

At least one technique has been developed for detecting PMT within a biventricular system so that biventricular pacing can then be suspended. See U.S. Patent Application US2001/0005790 to Ripart, published Jun. 28, 2001, which describes a technique for detecting PMT primarily based on changes in heart rate so that, for example, pacing in one of the ventricles can then be suspended to thereby break the PMT. Although the technique of Ripart may be capable of detecting certain types of PMT once it has occurred, it would be far preferable to provide techniques for actually preventing the onset of PMT within biventricular systems so that biventricular pacing need not be suspended but instead can be performed more or less continuously.

Accordingly, it would be desirable to provide techniques for reducing the risk of onset of PMT within biventricular pacing systems and it is to this end that aspects of invention are generally directed. In addition, to the extent that the technique of Ripart detects PMT once it has already occurred, it appears to do so primarily based on detection of a high heart rate in combination with a sudden rate increase. Hence, it may not be effective in detecting certain types of PMT, such as relatively lower rate PMT or PMT that is not associated with any sudden rate increase. Accordingly, it would also be desirable to provide improved techniques for detecting and terminating PMT once it has already occurred within a biventricular pacing system and it is to this end that other aspects of invention are directed.

Insofar as the prevention of PMT is concerned, because of the additional sensing channels used in biventricular systems, techniques that are effective for preventing PMT within a dual-chambered pacemaker may not work effectively and so various types of PMTs may nevertheless arise. For example, PMT can occur within a biventricular pacing system as a result of T-waves from the ventricles being detected on the atrial channel and being interpreted by the dual chamber pacemaker as an intrinsic P-wave, which in turn triggers a premature V-pulse in the ventricles. More specifically, whenever an intrinsic P-wave is detected on the atrial channel, the pacemaker is programmed to wait a predetermined amount of time for detection of an R-wave on the ventricular channels. If no R-wave is detected, the logic of the biventricular pacing system concludes that the ventricles failed to depolarize properly and a pair of V-pulses are delivered to the left and right ventricles, synchronized as needed. However, because the signal detected on the atrial channel was not actually an intrinsic P-wave, the ventricles will not likely depolarize within the expected period of time and so no R-wave will be detected on ventricular channels within the period of time. Accordingly, premature V-pulses will be delivered to the left and right ventricles, triggering another T-wave that likely causes another false detection of a P-wave on the atrial channel, thus triggering yet another pair of premature V-pulses. This process can continue indefinitely causing the heart to beat at the rate determined by the rate of the premature V-pulses and, hence, PMT occurs.

Conventionally, within dual-chambered devices, to prevent this form of PMT, a post ventricular atrial refractory period (PVARP) is applied to the atrial channel immediately following the delivery of a V-pulse to the right ventricle. During the PVARP, the device does not respond to any electrical events sensed on the atrial channel and so the device does not misinterpret a far field T-wave as an intrinsic P-wave. However, within a biventricular pacing system, the use of a PVARP is problematic. If the PVARP is initiated simultaneously with the first of the two ventricular pulses, the PVARP may have already expired before the T-wave propagates into the atria. Hence, this signal may be detected and misinterpreted as an intrinsic P-wave, thus triggering PMT. This is also referred to as T-wave oversensing.

Accordingly, it would be particularly desirable to provide techniques for preventing the onset of PMT within biventricular pacing systems by preventing false detection of intrinsic P-waves on the atrial channel and it is to this end that further aspects of invention are directed.

In another example of PMT within biventricular pacing systems, a T-wave associated with a V-pulse delivered to the right ventricle is erroneously detected on the left ventricular channel as an R-wave. Biventricular-triggered pacing systems are typically programmed to deliver a V-pulse to the left ventricle a fixed period of time (e.g. 20 milliseconds (ms)) following detection of an R-wave on the right ventricular channel to better synchronize the left and right ventricles. A refractory period (typically 300 ms) is then applied to the right ventricular channel. However, the resulting T-wave may be large in magnitude and fall outside the refractory period where it is then sensed on the right ventricular channel and misinterpreted as an intrinsic R-wave. If so, the device then delivers another V-pulse to the left ventricle shortly thereafter.

The pacing pulse delivered to the left ventricle will eventually trigger another T-wave, which will also probably be misinterpreted as an R-wave on the right ventricular channel, triggering yet another V-pulse in the left ventricle and PMT thereby ensues in an endless loop.

Accordingly, it would also be particularly desirable to provide techniques for preventing the onset of PMT within biventricular pacing systems by preventing false detection of intrinsic R-waves on the ventricular channels and it is to this and that still other aspects of invention are directed.

SUMMARY

In accordance with the invention, an implantable cardiac stimulation device is provided for implant within a patient wherein the device includes a biventricular pacing system operative to deliver biventricular pacing to the heart of the patient and a pacemaker mediated tachycardia (PMT) prevention system operative to control the biventricular pacing system to reduce the risk of onset of PMT. By providing a PMT prevention system along with a biventricular pacing system, the advantages of biventricular pacing may be achieved while reducing the risk of PMT and, in particular, reducing the risk of a ventricular tachycardia. Moreover, by preventing the onset of PMT during biventricular pacing, rather than merely detecting PMT (so that biventricular pacing can be suspended until the PMT terminates), biventricular pacing can be performed more or less continuously.

In a first exemplary embodiment, the PMT prevention system controls biventricular pacing so as to reduce the risk of onset by PMT by adjusting the timing of a PVARP applied by the biventricular pacing system so that that PVARP is synchronized with delivery of a second pulse of a pair of biventricular pacing pulses. Hence, if a left ventricular pacing pulse is delivered shortly after a right ventricular pacing pulse, the PVARP is synchronized with the left ventricular pacing pulse rather than the right ventricular pacing pulse. As noted above, PMT can occur as a result of the depolarization of the ventricles causing the atria to depolarize prematurely, which, in turn, may be erroneously detected as an intrinsic P-wave on the atrial channel, thus triggering a premature R-wave, in a repeating sequence. By synchronizing the PVARP with the second of the two ventricular pulses, the PVARP more effectively covers both the portion of the R-wave triggered by the right ventricular pulse and the portion triggered by the left ventricular pulse. If, on the other hand, the PVARP were instead synchronized with the first pulse, then the PVARP might expire before the portion of the R-wave triggered with the second ventricular pulse propagates into the atria. In this manner, more effective coverage of far field R-waves on the atrial channel is achieved without the need to lengthen the PVARP and the risk of this type of PMT is thereby reduced.

In accordance with a second exemplary embodiment, the PMT prevention system controls biventricular pacing so as to reduce the risk of onset by PMT by decreasing a sensitivity of an atrial sensing channel used by the biventricular pacing system during periods of ventricular repolarization (i.e. during T-waves) as detected on a ventricular channel. One specific technique for detecting T-waves is to rectify and combine the left and right ventricular channel signals and then to identify the T-waves based upon the combined signals. In any case, the sensitivity on the atrial channel is reduced during T-waves to reduce the likelihood of onset of PMT. As noted, oversensing of T-waves on the atrial channel can result in PMT because the device may erroneously interpret T-waves as being intrinsic P-waves, thus triggering delivery of a ventricular pulse soon thereafter although none is required. By reducing the atrial channel sensitivity during T-waves, it is less likely that the T-waves will be sensed on the atrial channel and so the risk of this type of PMT is reduced. Nevertheless, since the atrial channel sensitivity is merely reduced, other intrinsic electrical events can still be detected on the atrial channel, including true P-waves should one happen to occur during that time period. Hence, advantages are gained over techniques that might operate to apply a blanking interval to the atrial channel during T-waves.

In accordance with a third exemplary embodiment, particularly for use with triggered biventricular systems, the PMT prevention system controls biventricular pacing so as to reduce a risk of onset of PMT by enabling triggered ventricular pacing only following ventricular events that match a template representative of intrinsic ventricular depolarization events (i.e. that match a template of true R-waves.) Hence, only events matching the template (i.e. true R-waves) will trigger or inhibit pacing in the opposing ventricular chamber. This provides a technique for preventing T-wave oversensing on the ventricular channels from triggering PMT. As noted above, T-waves sensed on the right ventricular channel can be misinterpreted as R-waves, thus triggering a pacing pulse in the left ventricle, causing another T-wave, which in turn erroneously triggers another LV pulse, thus resulting in PMT. In one specific example, the R-wave templates are generated based on actual R-waves sensed within the heart of the patient and are adjusted, as needed, based on the heart rate of the patient. Preferably, the template matching system periodically modifies the shape of the template, if needed, to account for any changes in the shape of R-waves within the patient, which may occur because of new medications taken by the patient or perhaps because of the progression of heart disease.

In accordance with a fourth embodiment, the PMT prevention system controls biventricular pacing so as to reduce a risk of onset of PMT by controlling the biventricular pacing system to only track events occurring outside of a ventricular repolarization window (i.e. a T-wave window). In one example, a T-wave window is activated on both the atrial and ventricular channels following any paced or sensed event within either the left or right ventricular channel signals. Any event within the T-wave window is deemed to be a T-wave and not tracked, thereby helping to prevent T-wave oversensing of the type that can trigger PMT.

In accordance with fifth and sixth embodiments of the invention, the implantable cardiac stimulation device additionally includes a PMT detection and termination system operative to detect PMT and to then control the biventricular pacing system to terminate the PMT. Thus should PMT nevertheless arise, it can be detected and terminated, without needing to suspend biventricular pacing.

In the fifth embodiment, the PMT detection and termination system detects PMT based on a degree of variation in intervals between ventricular pulses and subsequent atrial depolarization signals (e.g. a RV-pulse to P-wave (VP) interval). As noted, the detection of far field T-waves on the atrial channel can be misinterpreted as sinus P-waves, thus triggering delivery of V-pulses on the ventricular channel a fixed period of time later. Thus, each V-pulse triggers a T-wave, which is misinterpreted as a P-wave, in turn triggering another V-pulse in a continuous cycle of PMT. Since this type of PMT imposes a fixed interval between V-pulses and detected P-waves, the onset of PMT can be detected based on the amount of variation in the V-pulse to P-wave intervals. In one example, if the interval falls below a predetermined threshold, PMT is deemed to have occurred and appropriate steps are taken, such as increasing the length of a PVARP, in an attempt to terminate the PMT. By expanding the PVARP of atrial channel, the far field T-waves are more likely to be covered by the refractory period and thereby not misinterpreted as a sinus P-wave, thus breaking the PMT cycle, without needing to suspend biventricular pacing.

In the sixth embodiment, for use with triggered biventricular systems, the PMT detection and termination system detects PMT based on a degree of variation in intervals within biventricular pacing cycles (e.g. an LV-pulse to LV-pulse interval). Again, if the interval falls below a predetermined threshold, PMT is deemed to have occurred and appropriate steps are taken, such as increasing the length of a PVARP. Hence, this sixth exemplary embodiment is similar to the fifth but is based on ventricular pacing intervals (LV/LV or RV/RV) rather than V-P intervals. If a T-wave from the left ventricle is sensed and misinterpreted as an intrinsic R-wave on the right ventricular channel, the biventricular pacing system will automatically triggered an LV pulse a fixed period time later. The LV pulse will then generate another T-wave also likely to be misinterpreted as an R-wave on the RV channel, triggering yet another LV pulse and PMT thereby ensues with a fixed ventricular pacing interval. By expanding refractory periods on the ventricular channels, a far field T-wave from an opposing ventricular chamber is more likely to be covered by the refractory period and thereby not misinterpreted as an intrinsic R-wave, thus breaking the PMT cycle, without needing to suspend biventricular pacing. This embodiment is particularly suitable for use within modes wherein there is no atrial sensing because either there is no atrial lead or the patient is in atrial fibrillation and so the implantable device has mode-switched to a non-atrial tracking mode.

Additional aspects of the invention are directed to detecting and terminating PMT within biventricular systems, without necessarily first taking steps to prevent the onset of PMT.

Thus, the invention provides various techniques for helping to prevent the onset of PMT within a biventricular pacing system and for detecting and terminating PMT if it nevertheless occurs. Other advantages and features of the invention are described below.

BRIEF DESCRIPTION OF THE DRAWINGS

Further features and advantages of the present invention may be more readily understood by reference to the following description taken in conjunction with the accompanying drawings, in which.

DETAILED DESCRIPTION OF ILLUSTRATIVE EMBODIMENTS

The following description is of the best mode presently contemplated for practicing the invention. This description is not to be taken in a limiting sense but is provided merely for the purpose of describing the general principles of the invention. The scope of the invention should be ascertained with reference to the issued claims. In the description of the invention that follows, like numerals or reference designators will be used to refer to like parts or elements throughout.

Figure 1:
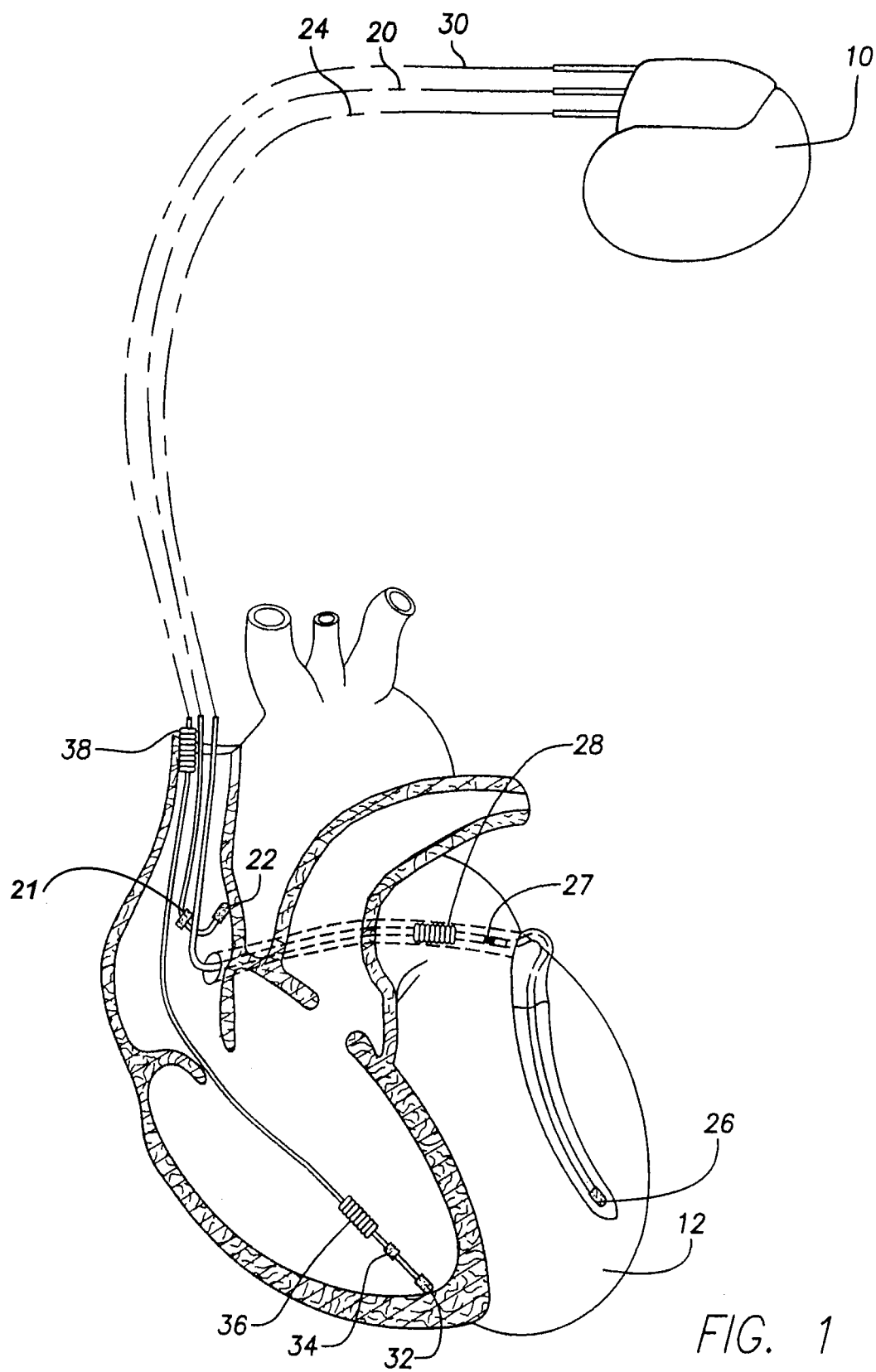
FIG. 1 is a simplified diagram illustrating an implantable stimulation device in electrical communication with at least three leads implanted into the heart of a patient for delivering multi-chamber stimulation and shock therapy and configured in accordance with the invention to perform overdrive pacing.
Figure 2:
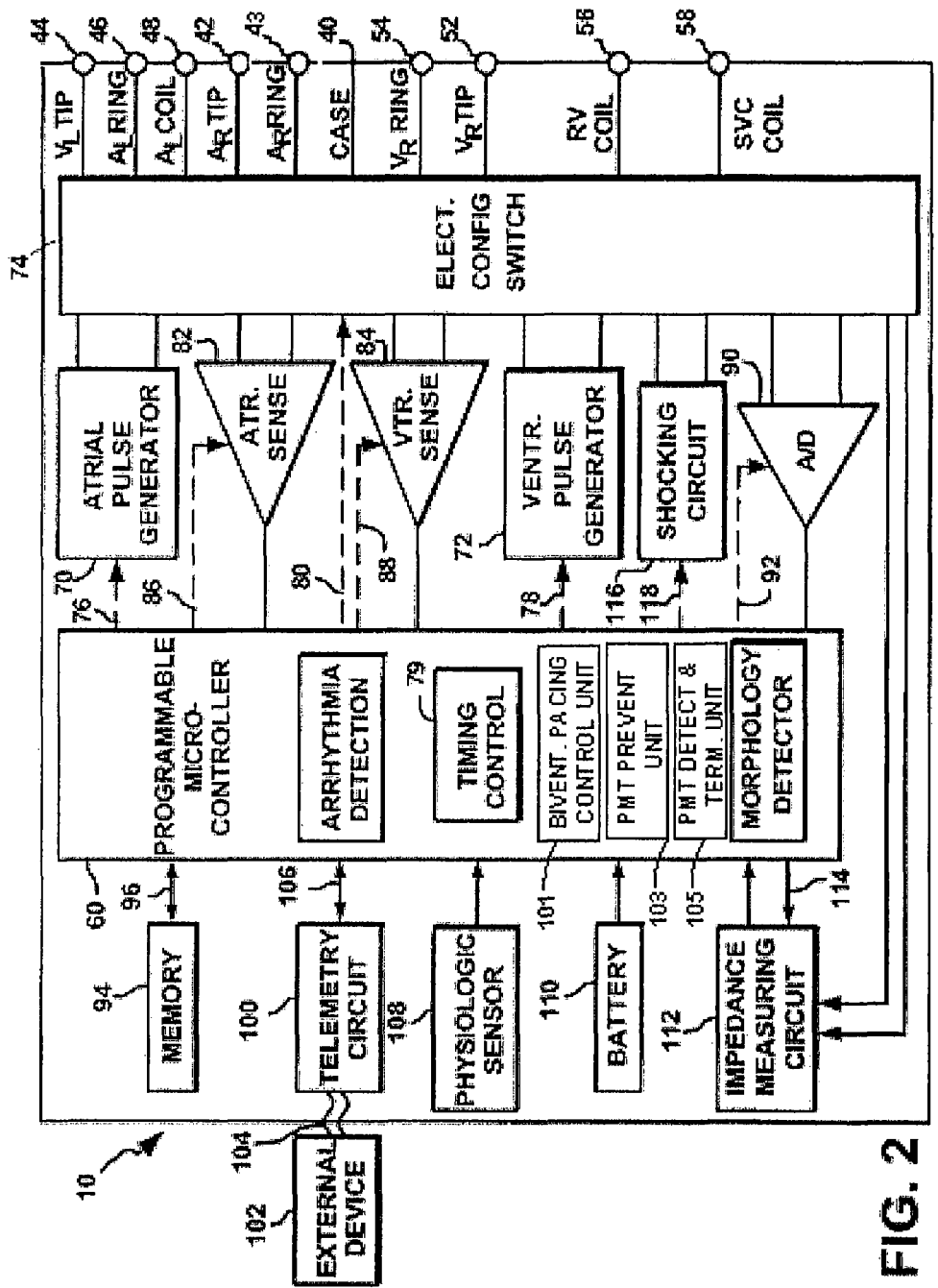
FIG. 2 is a functional block diagram of the implantable cardiac stimulation device of FIG. 1 illustrating basic elements of a stimulation device and particularly illustrating a PMT prevention unit.

The invention may be implemented using the implantable cardiac stimulation device illustrated in FIGS. 1 and 2. An overview of the stimulation device is provided, followed by a detailed description of the method of the invention.

Implantable Device Overview

In FIG. 1, a simplified block diagram is shown of a dual-chamber implantable stimulation device 10, which is capable of treating both fast and slow arrhythmias with stimulation therapy, including cardioversion, defibrillation, and pacing stimulation. To provide atrial chamber pacing stimulation and sensing, the stimulation device 10 is shown in electrical communication with a patient's heart 12 by way of an implantable unipolar atrial lead 20 having an atrial tip electrode 22 implanted in the patient's atrial appendage. The stimulation device 10 is also in electrical communication with the patient's heart 12 by way of an implantable bipolar ventricular lead 30 having, in this embodiment, a ventricular tip electrode 32, a right ventricular ring electrode 34, a right ventricular (RV) coil electrode 36, and a superior vena cava (SVC) coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle. With this configuration, biventricular pacing can be performed.

The right atrial lead 20 supports an atrial tip electrode 22, which is typically implanted in the patient's right atrial appendage. The right atrial lead 20 also supports a right atria ring electrode 21, which enables the device to sense atrial cardiac signals and apply pacing therapy to the right atrial chamber.

The coronary sinus lead 24 positions a left ventricular tip electrode 26 adjacent to the left ventricle and/or additional electrode(s) adjacent to the left atrium, such as a left atrial ring electrode 27 and a left atrial coil electrode 28. The coronary sinus lead 28 enables the device 10 to sense left atrial and ventricular signals and administer left chamber pacing therapy. In the illustrated arrangement, the left ventricular tip electrode 26 is used to sense atrial and ventricular signals and deliver left ventricular pacing therapy.

While a unipolar LV tip electrode 26 is shown in FIG. 1, it is to be understood that a bipolar LV electrodes could alternatively be employed. Also, although only three leads are shown in FIG. 1, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Referring now to FIG. 2, pertinent components of device 10 are described. Housing 40 (shown schematically) for the stimulation device 10 includes a connector (not shown) having an atrial tip terminal 42 adapted for connection to the atrial tip electrode 22 and a atrial ring terminal 43 of the atrial lead 20. The connector further includes a right ventricular tip terminal 52, a ring ventricular ring terminal 54, an RV shocking terminal 56, and an SVC shocking terminal 58 all of which are adapted for connection to the ventricular tip electrode 32, the right ventricular ring electrode 34, the RV coil electrode 36, and the SVC coil electrode 38, respectively. The housing 40 (often referred to as the "can", "case" or "case electrode") acts as the return (common) electrode, or anode, for both the atrial tip electrode 22 and the ventricular tip electrode 32 during unipolar sensing and as the return electrode for just the ventricular tip electrode 32 during combipolar sensing. Housing 40 can also act as the return (common) electrode, or anode, for the RV coil electrode 36, and the SVC coil electrode 38. For convenience, the names of the electrodes are shown next to the terminals. The left ventricular tip electrode 26, left atrial ring electrode 27, left atrial coil electrode 28, are adapted to be connected to the left ventricular tip terminal 44, left atrial ring terminal 46, and the left atrial coil terminal 48, respectively.

At the core of the stimulation device 10 is a programmable microcontroller 60, which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

Among other internal components, the microcontroller includes a biventricular pacing control unit 101 for controlling biventricular pacing, and a PMT prevention unit 103 for helping to prevent the onset of PMT during biventricular pacing. The PMT prevention unit operates in accordance with techniques described in detail below with reference to FIGS. 3-10. The microcontroller also includes a PMT detection and termination unit 105 for detecting PMT should it nevertheless arise during biventricular pacing and for controlling biventricular pacing so as to terminate the PMT, in accordance with techniques described in detail below with reference to FIGS. 11-14.

As shown in FIG. 2, an atrial pulse generator 70 and a ventricular pulse generator 72 generate pacing stimulation pulses for delivery by the atrial lead 20 and the ventricular lead 30, respectively, via a switch bank 74. Ventricular pulse generator is capable of generating separate pulses for delivery to the right and left ventricles in accordance with biventricular pacing techniques. The pulse generators, 70 and 72, are controlled by the microcontroller 60 via appropriate control signals, 76 and 78, respectively, to trigger or inhibit the stimulation pulses. The microcontroller 60 further includes a timing control unit that controls the operation of the stimulation device timing of such stimulation pulses that is known in the art. The microcontroller 60 may also include an autocapture threshold detection system, though autocapture threshold detection system is not necessary for the purposes of the invention.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, sets the polarity of the stimulation pulses by selectively closing the appropriate combination of switches (not shown) as is known in the art.

An atrial sense amplifier 82 and a ventricular sense amplifier 84 are also coupled to the atrial and ventricular leads 20 and 30, respectively, through the switch bank 74 for detecting the presence of cardiac activity. Sense amplifier 84 is capable of separately sensing signals from both the right and left ventricles in accordance with biventricular pacing techniques. The switch bank 74 determines the "sensing polarity" of the cardiac signal by selectively closing the appropriate switches, as is also known in the art. In this way, the clinician may program the sensing polarity independent of the stimulation polarity. The switch bank also permits the pacemaker to be set to either unipolar sensing or Combipolar sensing. For unipolar sensing, the V TIP and CASE terminals are connected to the ventricular sense amplifier for sensing a voltage differential there between and the A TIP and CASE terminals are connected to the atrial sense amplifier for sensing a voltage differential there between. For Combipolar sensing, the V TIP and CASE terminals are likewise connected to the ventricular sense amplifier but the A TIP and V TIP terminals are connected to the atrial sense amplifier for sensing a voltage differential between the tips of the atrial and ventricular leads.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation. The gain control is actuated by the programmable micro controller 60. The gains are controlled on the ventricular sense amplifier 84 by the microcontroller using control line 88 and on the atrial sense amplifier 82 on control line 86. The outputs of the atrial and ventricular sense amplifiers, 82 and 84, are connected to the microcontroller 60 which, in turn, inhibits the atrial and ventricular pulse generators, 70 and 72, respectively, in a demand fashion whenever cardiac activity is sensed in the respective chambers.

For arrhythmia detection, the invention utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P-P and R-R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, activation of special algorithms such as automatic mode switch or high atrial rate episode logging, anti-tachycardia pacing, cardioversion shocks or defibrillation shocks, also known as "tiered therapy"). An arrhythmia detection unit of the microcontroller oversees arrhythmia detection.

Cardiac signals are also applied to the inputs of an analog to digital (A/D) data acquisition system 90. In order to match the signal amplitude and/or the resolution to a range appropriate for the function of the A/D converter 90, the gain of the A/D converter is controlled by the microprocessor 60 using a control line 92. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108. Such sensors are commonly called "rate-responsive" sensors. The physiological sensor 108 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the invention and is shown only for completeness. The stimulation device additionally includes a battery 110 that provides operating power to all of the circuits shown in FIG. 2. For the stimulation device 10, which employs shocking therapy, the battery must be capable of operating at low current drains for long periods of time and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the present invention preferably employs lithium/silver vanadium oxide batteries, as is true for most (if not all) such devices to date. As further shown in FIG. 2, the invention preferably includes an impedance measuring circuit 112, which is enabled by the microcontroller 60 by a control signal 114. The impedance measuring circuit 112 is not critical to the invention and is shown for only completeness.

Depending upon the implementation, the device may function as an implantable cardioverter/defibrillator (ICD) device. That is, if it detects the occurrence of an arrhythmia, it automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5 to 10 joules), or high energy (11 to 40 joules), as controlled by the microcontroller 60. Such shocking pulses are applied to the patient's heart through at least two shocking electrodes, as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 to 40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval.

VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

PMT Prevention Techniques

The remaining figures include flow charts and graphs illustrating improved techniques for preventing the onset of PMT within biventricular pacing systems and of detecting and terminating PMT if is should nevertheless arise. In the flow charts, the various steps of the methods are summarized in individual "blocks". Such blocks describe specific actions or decisions that are made or carried out as the method proceeds. The actions or decisions set forth in the various blocks are performed by components of the implantable device of FIG. 2 under the control of microcontroller 60, and particularly under the control of the biventricular pacing unit, PMT prevention unit, and PMT detection and termination unit of the microcontroller. The flow charts thus provide the basis for a "control program" that may be used to effectuate the desired control of the stimulation device. Those skilled in the art may readily write such a control program based on the flow charts and other descriptions presented herein. Various graphs are also provided, which illustrate exemplary atrial and ventricular IEGM signals. The graphs illustrate idealized representations of the signals. Actual IEGM signals will likely have quite different shapes, dependent, in part, on the particular location and configuration of the electrodes mounted in the heart and the particular sensing technique used (unipolar, bipolar etc.)

1. Synchronization of PVARP with Second Ventricular Pulse

Figure 3:
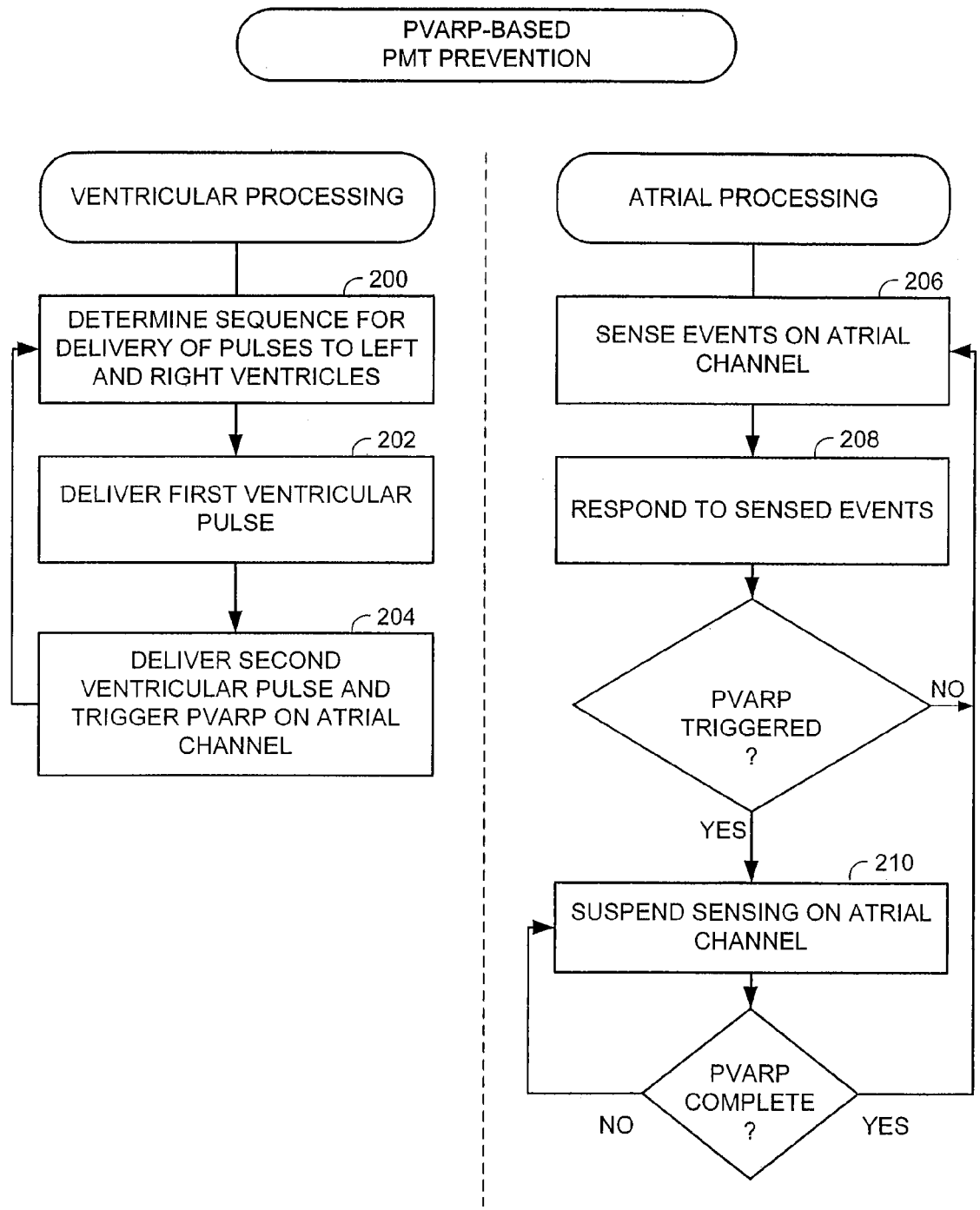
FIG. 3 is a flow chart providing an overview of the operation of a first exemplary embodiment of the invention particularly illustrating the manner by which the PMT prevention unit of the implantable stimulation device of FIGS. 1 and 2 operates to reduce the likelihood of PMT based on proper synchronization of PVARPs.

FIG. 3 illustrates, at a high-level, a technique for preventing the onset of PMT based on proper synchronization of the PVARP performed by the implantable device of FIG. 2. Within FIG. 3, processing of ventricular channel signals by the implantable device is illustrated on the left and processing of atrial channel signals is shown on the right. Initially, during step 200, ventricular channel signals are processed by the implantable device to determine the sequence for delivery of pulses to the left and right ventricles. In this regard, the implantable device determines the order by which the left and right ventricles are to be paced, as well as, the time delay therebetween. In one example, the right ventricle is paced about 30 milliseconds prior to the left ventricle. However, this time delay can be adjusted and, for some patients, it may be preferable to pace the left ventricle slightly before the right ventricle. In any case, at step 202, the implantable device delivers a first ventricular pulse to the appropriate chamber. At step 204, the implantable device delivers a second ventricular pulse to the opposing the ventricular chamber and triggers a PVARP on the atrial channel. Thus, the PVARP is synchronized with the second of the two ventricular pulses, rather than the first.

Meanwhile, on the atrial channel, electrical events are sensed beginning at step 206 and, at step 208, the implantable device responds to the sensed events in accordance with conventional biventricular pacing techniques. Since pacing is performed primarily in the ventricles, the response to events sensed within the atrial maybe limited to triggering various timing intervals. In addition, diagnostic information may be stored pertinent to the events sensed on the atrial channels. However, depending upon the particular programming of the pacing device, the atria may be paced as well, perhaps in accordance with dynamic atrial overdrive pacing techniques as described in, for example, U.S. Pat. No. 6,519,493, entitled "Methods And Apparatus For Overdrive Pacing Heart Tissue Using An Implantable Cardiac Stimulation Device" of Florio et al., issued Feb. 11, 2003. In any case, once the PVARP has been triggered at step 204 on the atrial channel, sensing on the atrial channel is suspended at step 210 for the duration of the PVARP. After the PVARP has expired, processing on the atrial channel resumes at step 206 where additional events are again sensed. The duration of the PVARP may be set in accordance with conventional techniques and may be split into a separate atrial blanking period (during which time the atrial sense amplifiers are deactivated and so no events are sensed whatsoever) and an atrial refractory period (during which the sense amplifiers are active for sensing events on the atrial channel, but the device does not respond to any events on the atrial channel).

Thus, FIG. 3 sets forth a technique for reducing the risk of onset of PMT wherein the PVARP is triggered based upon the second of the two ventricular pacing pulses. PMT can occur as a result of far field T-waves from the ventricles being detected in the atria, which is erroneously detected as an intrinsic P-wave, thus triggering a premature V-pulse. By triggering the PVARP upon delivery of the second V-pulse, the PVARP more effectively covers both the far field T-wave associated with the first ventricular pulse and the far field T-wave associated with the second ventricular pulse on the atrial channel. If, on the other hand, the PVARP was triggered based on the first of the ventricular pulses, then the PVARP may already have expired by the time the T-wave associated with the second ventricular pulse is generated and propagates to the atrial channel sensing locations. As an alternative, the duration of the PVARP could be expanded and timed to coincide with the first ventricular pulse. However, the longer PVARP could have adverse consequences such as improperly covering a subsequent true P-wave, particularly during high heart rates. Hence, it is preferable to maintain the standard duration of the PVARP, but synchronized with the second ventricular pulse rather than the first ventricular pulse.

Figure 4:
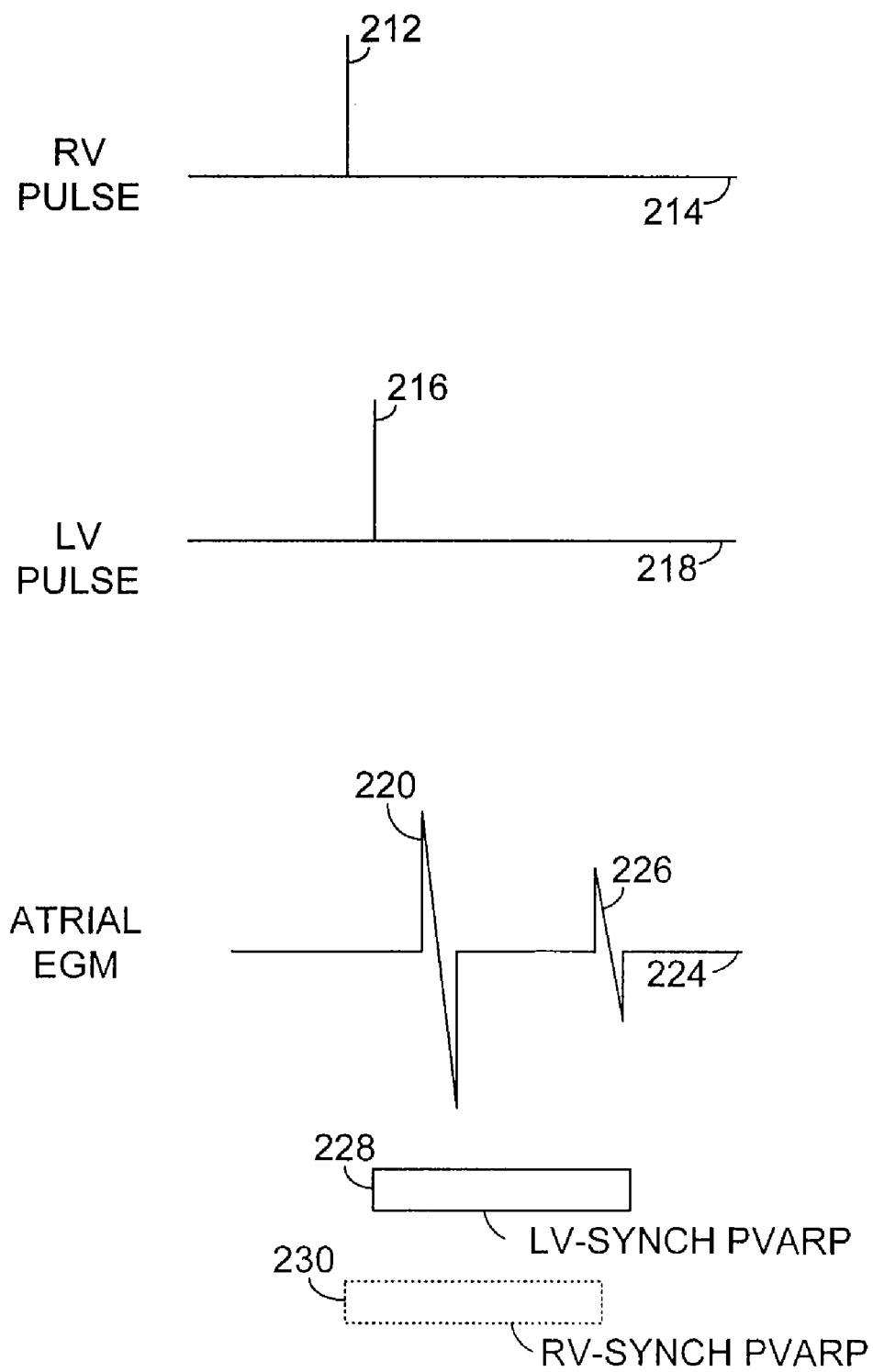
FIG. 4 is a graph illustrating the technique employed by the PVARP-based PMT prevention unit of FIG. 3.

This is illustrated within FIG. 4, which shows a first ventricular pulse 212 delivered via a right ventricular channel 214 and a second ventricular pulse 216 delivered via a left ventricular channel 218. The resulting far-field R-wave 220 and T-wave 222 are shown within an atrial channel EGM 224. In the example of FIG. 4, there is a resulting far field T-wave (222). With a PVARP 228 synchronized with delivery of the LV ventricular pulse 216, rather than the RV pulse 212, the far field T-wave 226 occurs during the PVARP and is therefore properly ignored on the atrial channel. Hence, T-wave 226 does not trigger (or inhibit) further biventricular pacing, such as delivery of another pair of V-pulses on the ventricular channel, which may, in turn, trigger yet another false P-wave, resulting in an endless cycle of PMT. FIG. 4 also illustrates, in phantom lines, a PVARP 230 triggered following the RV ventricular pulse. As can be seen, PVARP 230 would not completely cover the T-wave 226 permitting PMT to occur.

2. Reduced Sensitivity of Atrial Channel During T-Waves

Figure 5:
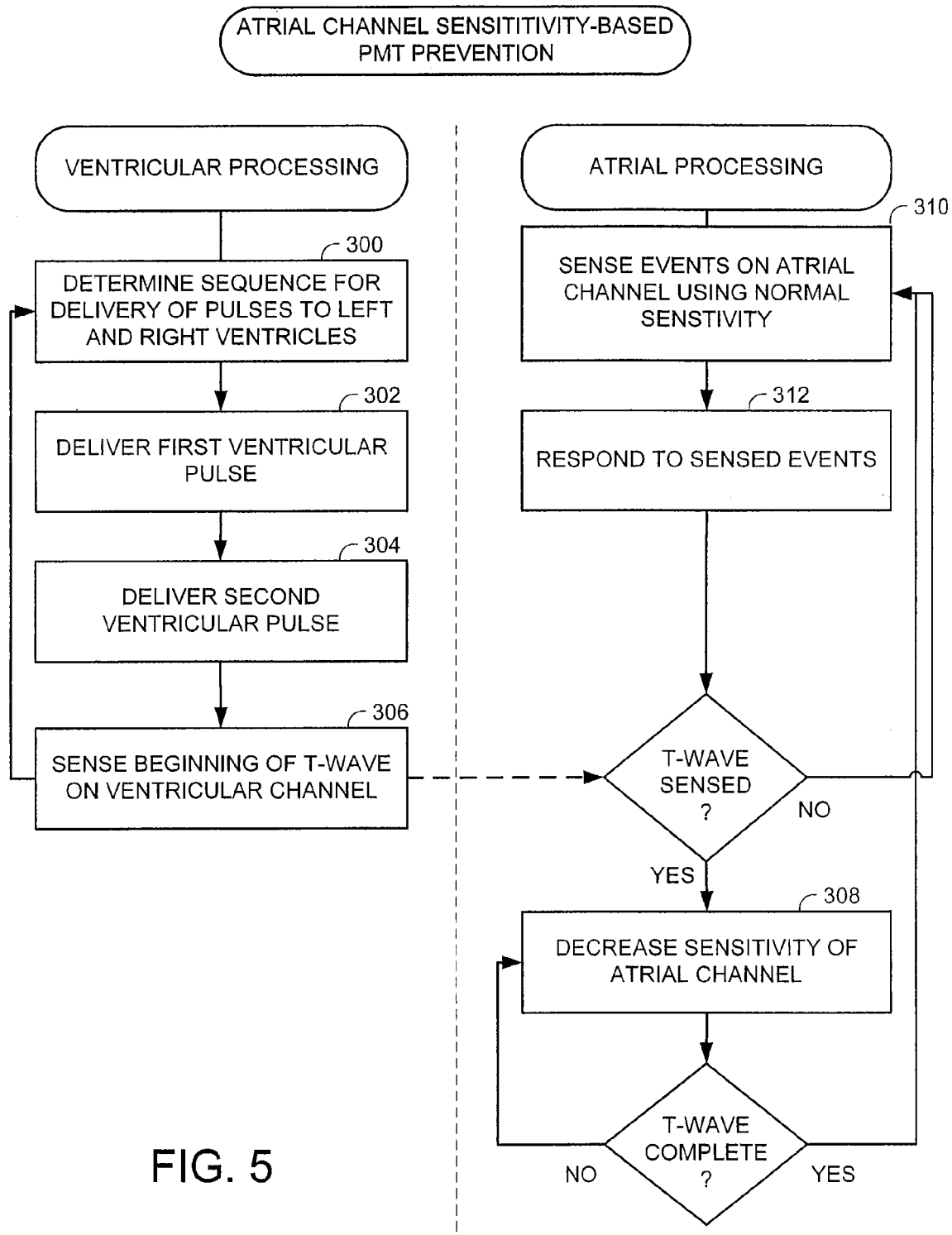
FIG. 5 is a flow chart providing an overview of the operation of a second exemplary embodiment of the invention and particularly illustrating the manner by which the PMT prevention unit of the implantable stimulation device of FIGS. 1 and 2 operates to reduce the likelihood of PMT by selectively reducing atrial channel sensitivity during T-waves.

FIG. 5 illustrates, at a high level, a technique for preventing the onset of PMT wherein the sensitivity of the atrial channel is decreased upon detection of a T-wave on the ventricular channel so that the T-wave will not erroneously be sensed on the atrial channel, which could induce PMT. On the ventricular channel, beginning at step 300, the device determines the sequence for delivery of pulses to the right and left ventricles.

Again, the device determines not only the order with which the pulses are to be delivered, but also the time delay therebetween. The first and second ventricular pulses are delivered at steps 302 and 304, respectively. Following delivery of the second ventricular pulse, the device awaits detection of a T-wave on the ventricular channel, at step 306. Upon detection of the T-wave, the sensitivity with which electrical events are sensed on the atrial channel is decreased, at step 308, for a predetermined period of time equal to the duration of the T-wave. In one example, the actual duration of the T-wave may be determined from the ventricular channel and then this value used on the atrial channel. Alternatively, an average duration of T-waves may be determined in advance, perhaps using a running average, with the average value then used as the duration of the T-wave blanking interval. In addition, preferably, the reduction in sensitivity of the atrial channel is delayed by an amount sufficient to account for the propagation time delay for electrical signals to travel from the ventricles to the atria. In any case, the atrial channel is less sensitive during the far field T-wave and hence will not likely detect the far field T-wave. Following the period of reduced sensitivity, atrial processing continues at step 310, wherein the device resumes sensing electrical events on the atrial channel using the normal sensitivity values. At step 312, the device responds to any events detected on the atrial channel to detect, for example, intrinsic P-waves so that ventricular pulses may be applied if an R-wave is not detected within an expected time period.

Thus, FIG. 5 illustrates a technique for reducing the sensitivity on the atrial channel during a time period corresponding to the T-wave on the ventricular channel for the purposes of reducing the likelihood of PMT. Erroneous detection of a far field T-wave on the atrial channel can result in PMT because the device may erroneously interpret the T-wave as being an intrinsic P-wave, thus triggering a ventricular pulse soon thereafter when none is actually required. Hence, each ventricular pulse may result in misdetection of a P-wave, which, in turn, triggers another ventricular pulse, in an endless cycle of PMT. By reducing the sensitivity of atrial channel, T-wave oversensing on the atrial channel is avoided and so the risk of PMT is reduced. However, because the atrial channel merely has reduced sensitivity, and is not completely blanked, other intrinsic electrical events can still be detected on the atrial channel during this period of time, including a true P-wave, should one occur at that time.

Figure 6:
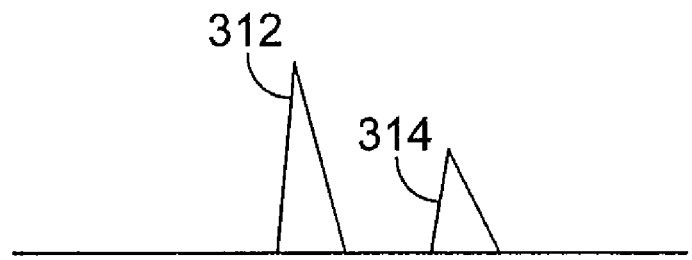
FIG. 6 is a graph further illustrating the technique of FIG. 5.
Figure 6:
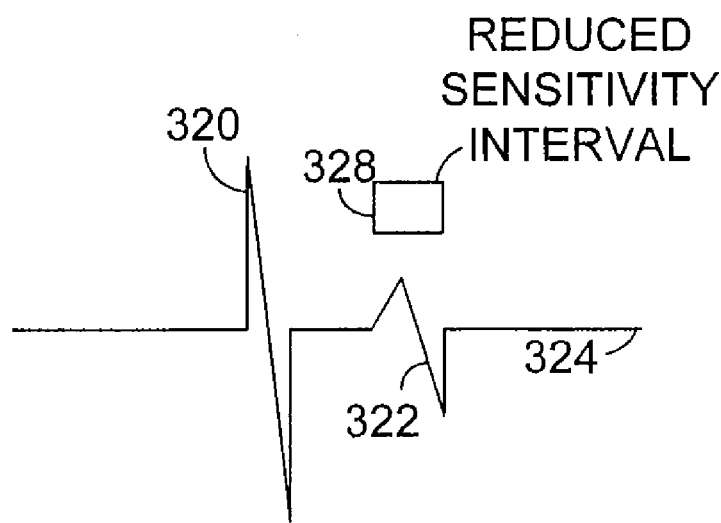

In one specific example, detection of T-waves is achieved by rectifying signals on both the left and right ventricular channels, then summing in the rectified signals. R-waves and T-waves are detected within the rectified signals and the atrial channel sensitivity is reduced during the T-wave. This is illustrated within FIG. 6, which shows idealized versions of the summed and rectified ventricular signals corresponding to an R-wave 312 and a T-wave 314. Also illustrated are the corresponding far-field R-wave 320 and T-wave 322 within an atrial channel EGM 324. In the example of FIG. 6, the far field T-wave (322), if detected, could be misinterpreted as a P-wave. However, with the sensitivity of the atrial channel reduced during an interval 328 corresponding to the T-wave as detected within the rectified signals, the far-field T-wave is not sensed and is therefore properly ignored on the atrial channel. (Note that when the channel sensitivity is decreased, the detection threshold is thereby increased, permitting detection of only events having a greater magnitude. When the channel sensitivity is increased, the detection threshold is thereby lowered permitting detection of events of lower magnitude as well.) In one example, the sensitivity on the atrial channel is decreased by 50% during the reduced sensitivity interval.

3. Template Matching to Avoid Vent. Channel Oversensing

Figure 7:
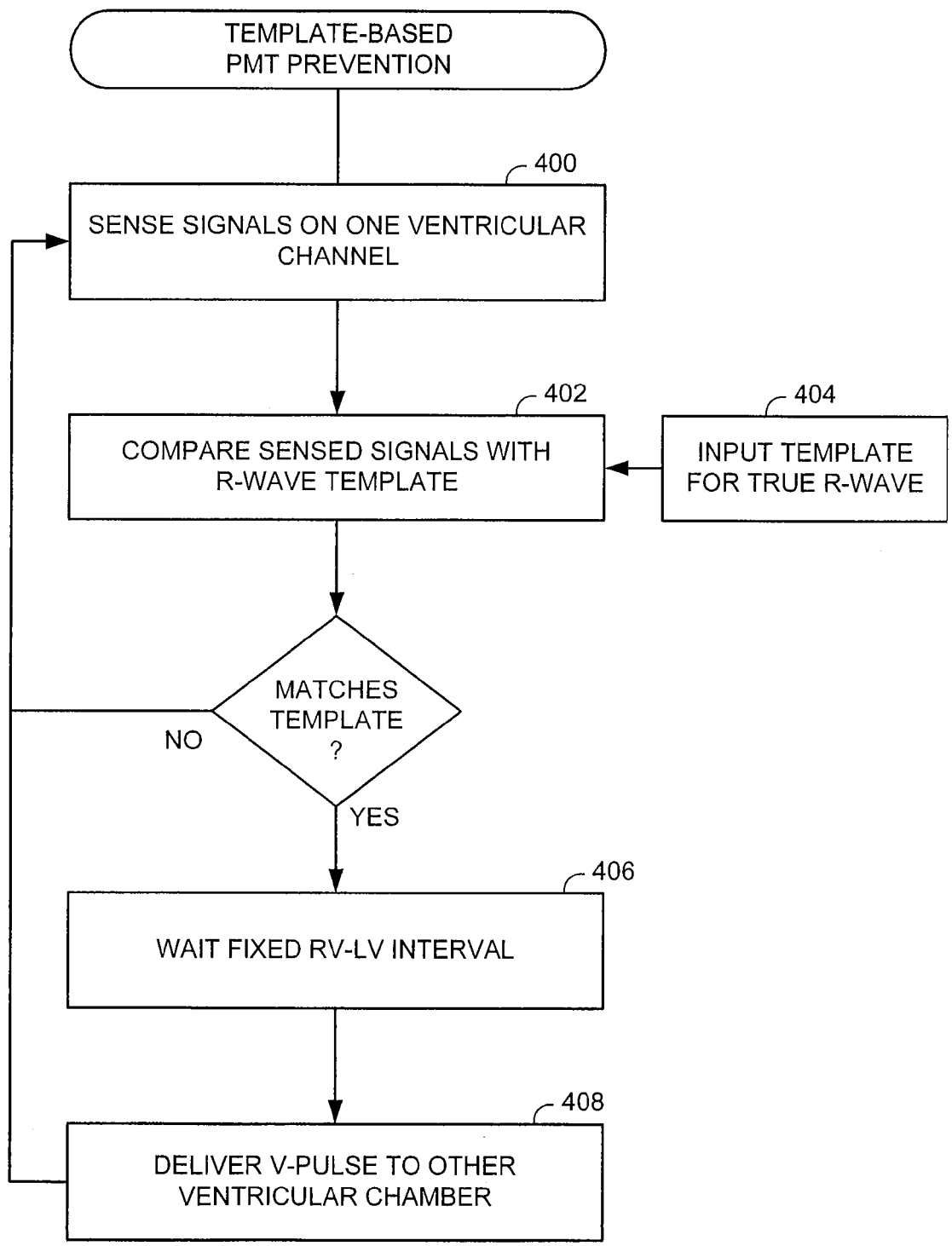
FIG. 7 is a flow chart providing an overview of the operation of a fifth exemplary embodiment of the invention and particularly illustrating the manner by which the PMT prevention unit of the implantable stimulation device of FIGS. 1 and 2 operates to reduce the likelihood of PMT based on R-wave template matching.

Referring now to FIG. 7, a technique for preventing the onset of PMT using for use within biventricular triggered pacing systems, which analyzes templates representative of true R-waves. As already noted, an example of a triggered biventricular system is one configured to automatically deliver a pacing pulse to the left ventricle shortly following detection of a right ventricular depolarization so as to synchronize the ventricles. In FIG. 7, all pertinent processing steps are performed in the ventricular channels and so separate atrial channel processing steps are not illustrated. At step 400, the device senses ventricular events in one of the ventricular channels, typically the right channel. At step 402, the sensed event is compared with a template representative of a true R-wave, input at step 404. If the sensed event matches the template, then the sensed event is designated as a true R-wave and the implantable device waits a fixed period of time (e.g. 20 ms), at step 406, then delivers a V-pulse to the opposing ventricular chamber, at step 408. On the other hand, if the sensed ventricular signals do not match the template following step 402, indicating that it is not a true R-wave, then the sensed R-wave is ignored and processing merely returns to step 400 for continued monitoring of the first ventricular channel for the purposes of detecting R-waves. In this manner, the ventricular channels are only responsive to true R-waves, rather than to far field T-waves or other electrical events.

Figure 8:
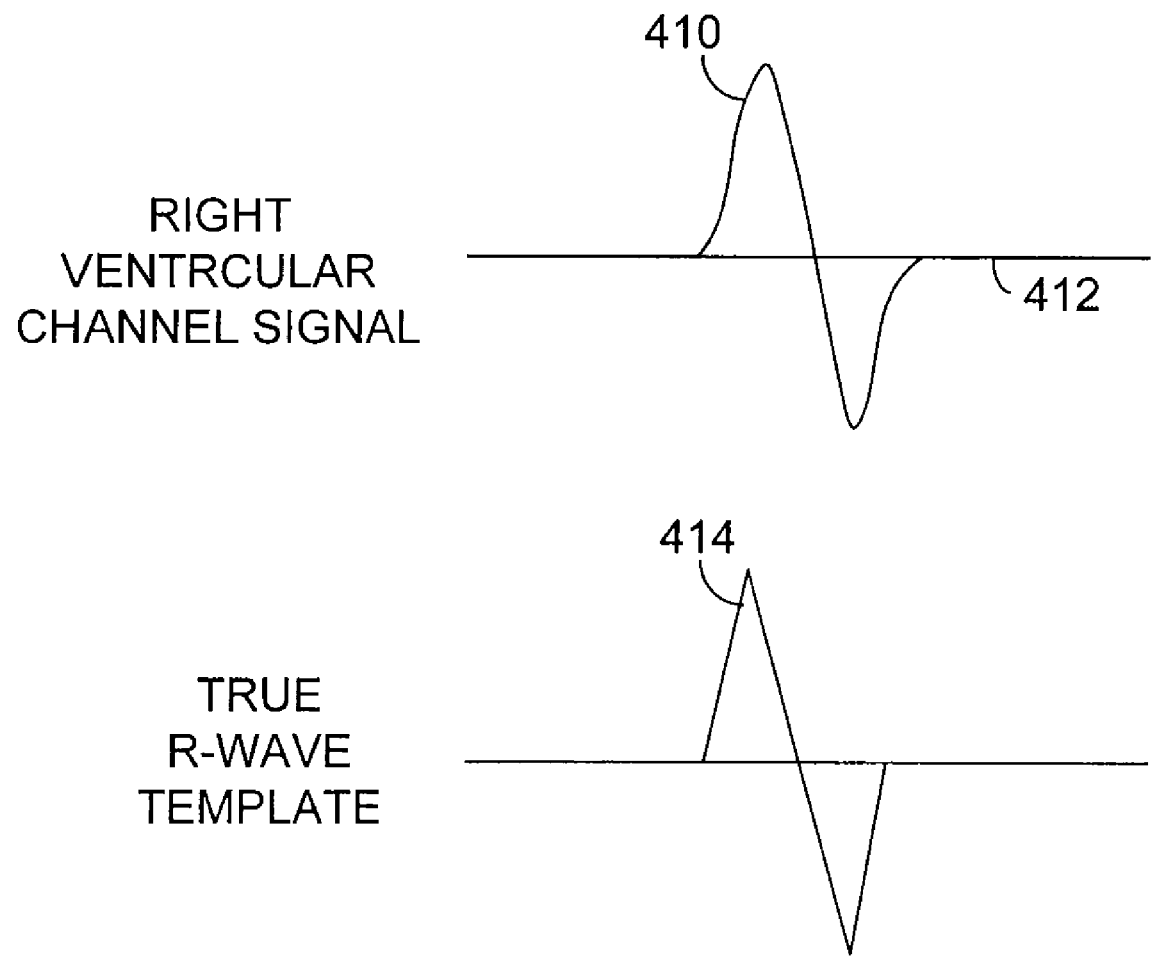
FIG. 8 is a graph further illustrating the technique of FIG. 7.

FIG. 8 illustrates an exemplary R-wave 410 sensed on the right ventricular channel 412 and a template 414 representative of a true (idealized) R-wave. In the example of FIG. 8, the sensed R-wave generally matches the template in size and shape and so it is designated as a true R-wave. Template matching may be performed in accordance with conventional techniques. The shape of the template may be adjusted based on the current heart rate or other factors. Preferably, the template is generated based on actual R-waves sensed within the heart of the patient in which the device is implanted. In this manner, the unique shapes of R-waves within individual patients are accounted. Preferably, the device periodically adjusts the shape of the template, if needed, to account for any changes in the shapes of R-waves within the patient, such as those arising because of new medications or perhaps because of progression of the heart disease. Template matching techniques are described in U.S. Pat. No. 5,779,645, to Olson et al., entitled "System and Method for Waveform Morphology Comparison," which is incorporated by reference herein.

Thus, the technique of FIG. 7 provides a method for preventing far field T-waves from being misinterpreted as R-waves on the opposing ventricular channel. T-waves sensed on the left ventricular channel can be misinterpreted as R-waves, thus triggering an LV pulse causing another far field T-wave, which in turn erroneously triggers another LV pulse, in an endless cycle of PMT. A similar template matching technique can be provided on the atrial channel for verifying that P-waves detected thereon are true P-waves, rather than far field signals from the ventricles.

4. T-Wave Blanking Windows to Prevent T-Wave Oversensing

Figure 9:
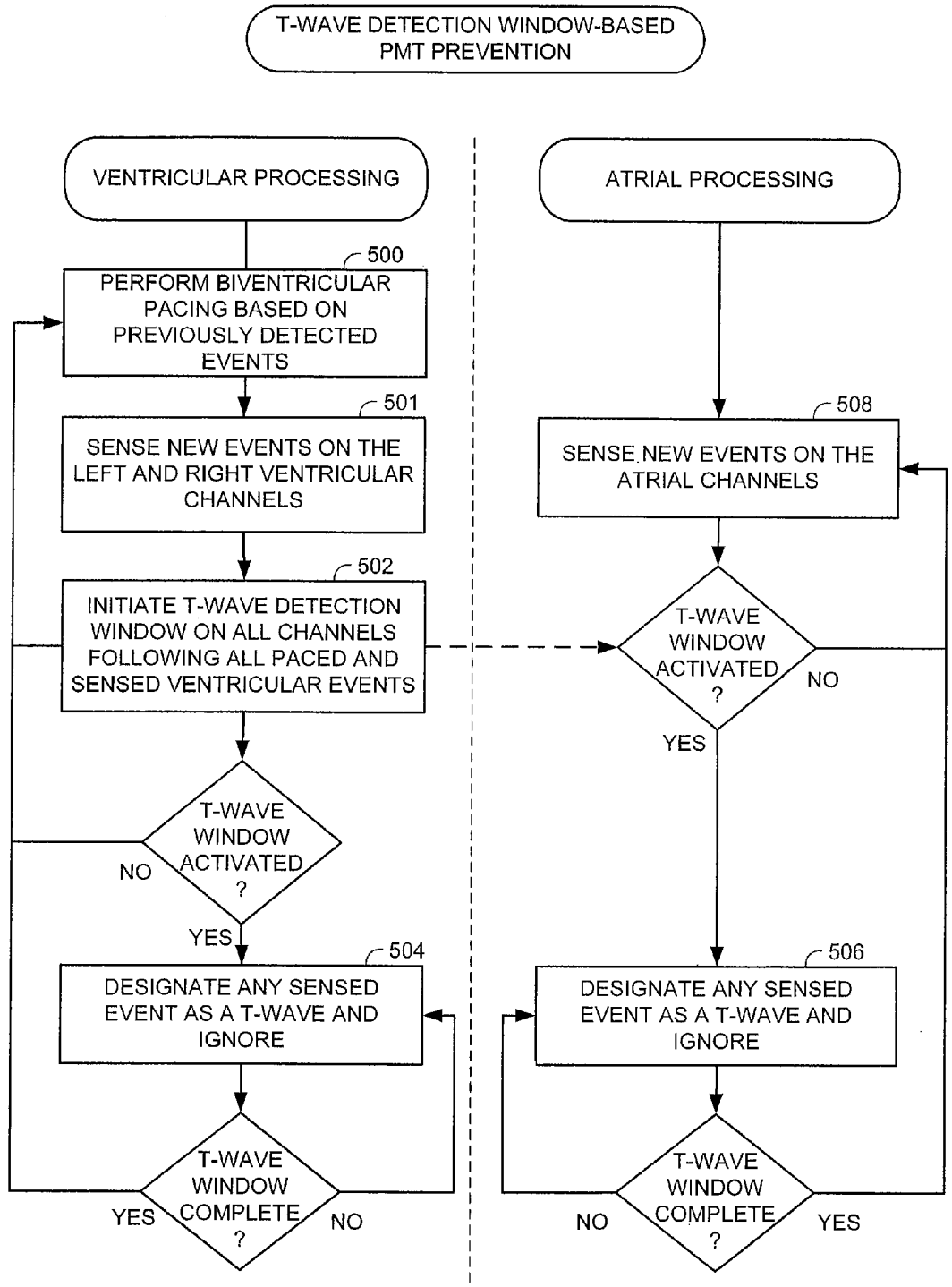
FIG. 9 is a flow chart providing an overview of the operation of a sixth exemplary embodiment of the invention and particularly illustrating the manner by which the PMT prevention unit of the implantable stimulation device of FIGS. 1 and 2 operates to reduce the likelihood of PMT based on the application of T-wave windows.

FIG. 9 illustrates a technique for preventing the onset of PMT, which employs a T-wave detection interval or window applied to both the ventricular channels and the atrial channels. As with FIGS. 3 and 5 above, ventricular channel processing is shown on the left and atrial channel processing is shown on the right. On the ventricular channel, beginning at step 500, the implantable device performs biventricular pacing based on previously detected events, such as P-waves and R-waves. At step 501, the implantable device senses new events on both the left and right ventricular channels. Following every paced or sensed ventricular event, detected on either the left or the right ventricular channels, the implantable device initiates a T-wave window, at step 502. The timing and duration of the T-wave window is set such that, if the paced or sensed event had been either a V-pulse or an R-wave, the T-wave window will cover the subsequent T-wave. Then, at steps 504 and 506, any events sensed during the T-wave window on either the ventricular channel or the atrial channel are deemed to be T-waves and ignored, at least for the purposes of triggering or inhibiting pacing, i.e. the T-wave is not tracked. The detected T-waves may be utilized for other purposes, though, such as for diagnostic purposes. Thus, the T-wave window is not a blanking window. Once the T-wave window on the ventricular channel has completed, processing returns to step 500 for additional biventricular pacing based on detected events. Likewise, once the T-wave window on the atrial channel has completed, execution proceeds to step 508 wherein the device senses new events on the atrial channel. Although not shown in FIG. 9, other atrial and ventricular windows, such as ventricular blanking intervals, PVARPs, etc., are also utilized along with the T-wave windows, in accordance with otherwise conventional techniques. Hence, in some cases, a T-wave window will occur during a ventricular refractory period or during a PVARP and will have no additional effect. In addition, when both LV and RV pulses are applied, T-wave windows are independently applied following both the LV and RV pulse. These windows may overlap.

Figure 10:
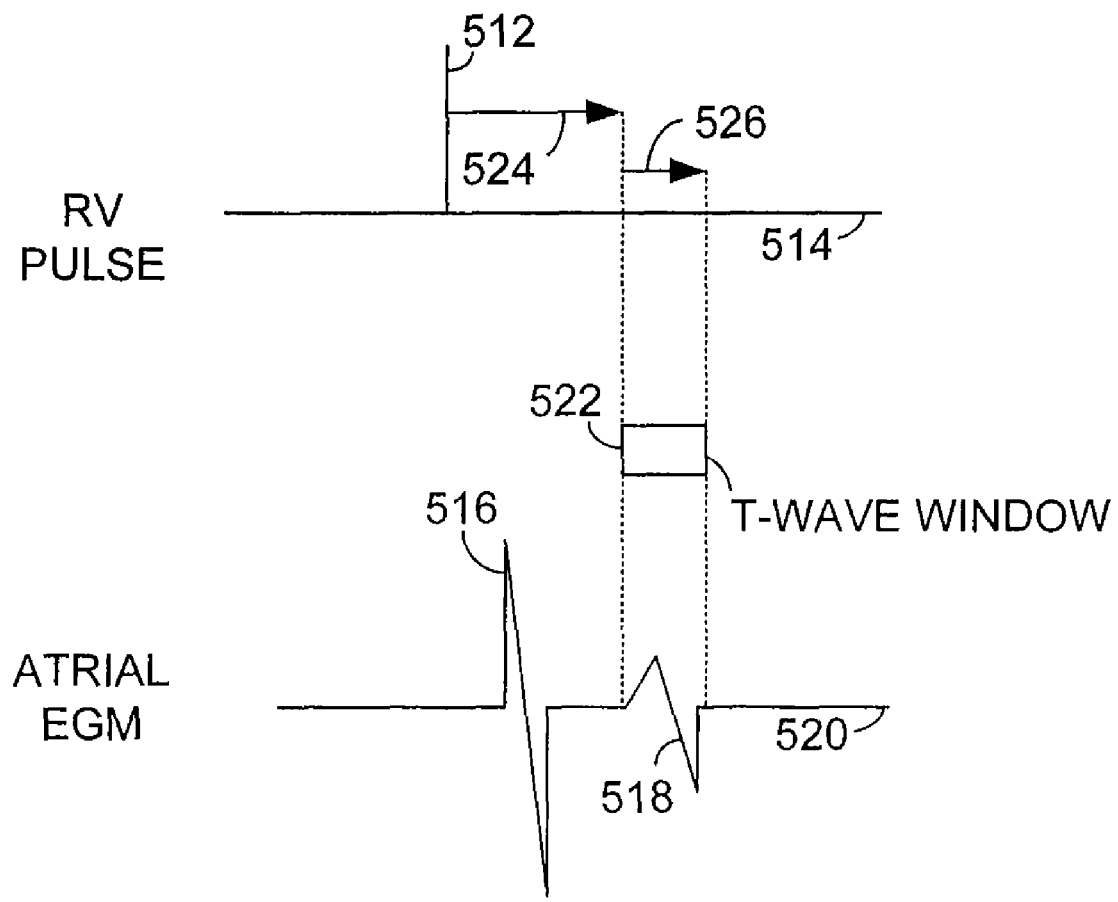
FIG. 10 is a graph further illustrating the technique of FIG. 9.

By designating all events sensed within the T-wave windows on the atrial or ventricular channels as T-waves, T-wave oversensing is avoided. Hence, various types of PMT that result from T-wave oversensing are avoided. For example, as noted above, if T-waves sensed on the atrial channel are misinterpreted as intrinsic P-waves, the pacing system may deliver unnecessary V-pulses to the ventricular channels, thus generating more T-waves, which may again be misinterpreted as P-waves, resulting in PMT. By applying T-wave windows on the atrial channel, true T-waves are thereby properly designated as T-waves and are not misinterpreted as P-waves, thus preventing this type of PMT. Also, by simply activating T-wave windows following all paced and sensed events on the ventricular channels, the system need not devote processing resources to trying to distinguish different types of sensed events before determining whether to activate a T-wave window. Rather any paced or sensed event on either the left or the right ventricular channel triggers a subsequent T-wave window on all channels. A T-wave window applied to the atrial channel is illustrated in FIG. 10, which shows a V-pulse 512 delivered via a right ventricular channel 514 and the resulting far field R-wave 516 and T-wave 518 appearing on the atrial channel. A T-wave window 522 is applied to the atrial channel and timed to cover far field T-wave 518. The time delay for the T-wave window, measured from the V-pulse, is shown by arrow 524 and the duration of the T-wave window, measured from the beginning of the window, is shown by arrow 526. As can be seen, the time delay and duration are such that the T-wave window covers the far field T-wave on the atrial channel, thereby ensuring that the T-wave will be properly identified as a T-wave and not misinterpreted as an intrinsic P-wave. Although not shown in FIG. 10, similar T-wave widows are applied to both the RV and LV channels.

Insofar as the timing and duration of the T-wave window is concerned, in one example, the implantable device is configured to continuously monitor the time delay between QRS complexes and subsequent T-waves (QT interval) and to monitor the duration of T-waves. The implantable device maintains running averages of the QT interval and T-wave duration and uses these averages for determining when to apply the next T-wave window. The time delay and duration of the T-wave windows applied to the right ventricular, left ventricular and atrial channels may differ to take into account electrical signal propagation delays within the heart. For example, the T-wave window applied to the atrial channel may be delayed by an amount sufficient to compensate for the time it takes electrical signals to propagate from the ventricles into the atria. Hence, the T-wave windows applied to the three channels need not be contemporaneous. Further details regarding techniques for determining the timing and duration of T-wave intervals is provided in U.S. patent application Ser. No. 10/033,410, filed Oct. 25, 2001, entitled, "Method And Apparatus For Blanking T-Waves From Combipolar Atrial Cardiac Signals Based On Expected T-Wave Locations" of McClure et al., which is assigned to the assignee of the present application and is incorporated by reference herein.

PMT Detection Techniques

1. V-P Interval-Based Detection

Figure 11:
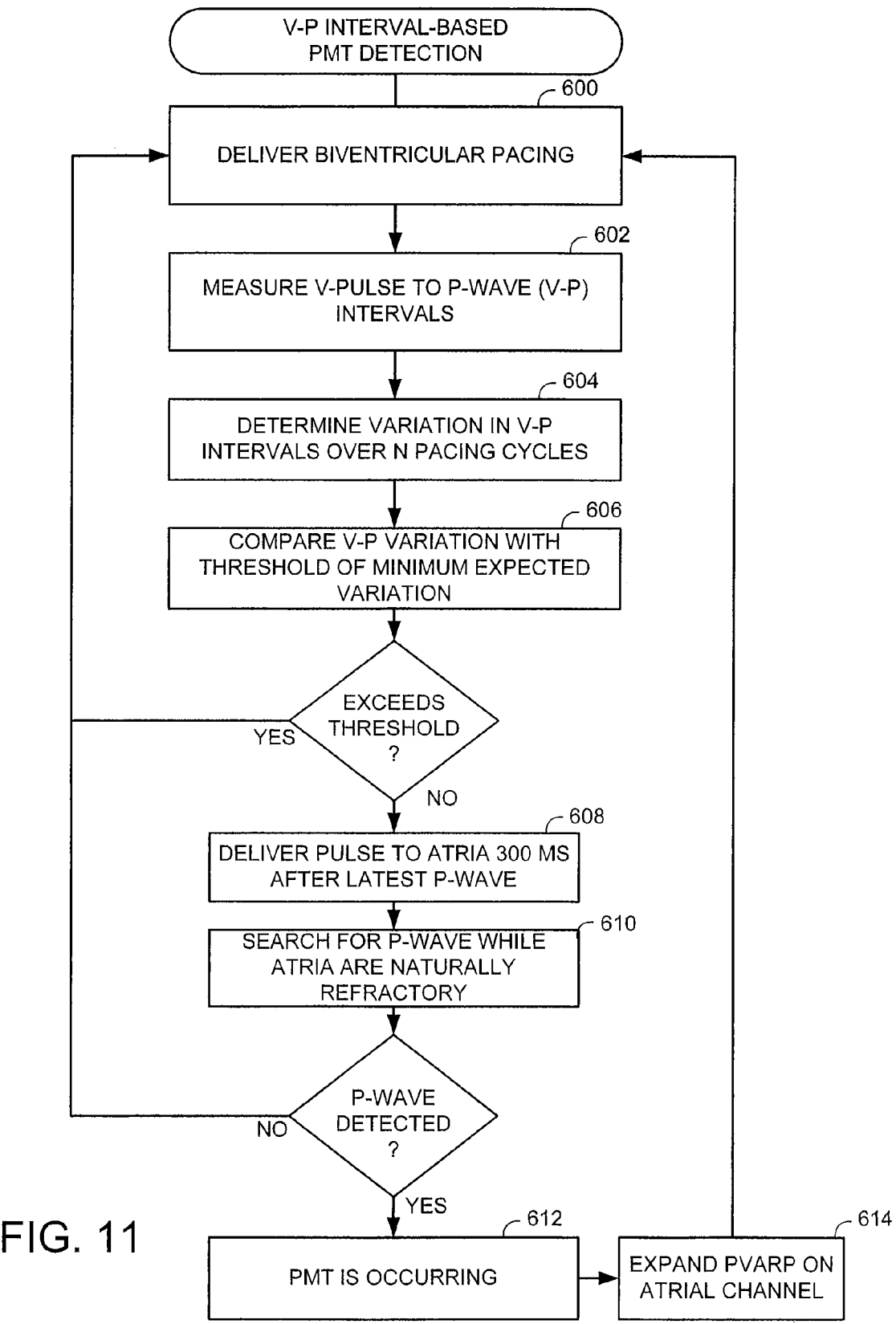
FIG. 11 is a flow chart providing an overview of the operation of a third exemplary embodiment of the invention and particularly illustrating the manner by which the PMT detection unit of the implantable stimulation device of FIGS. 1 and 2 operates to detect PMT based on a degree of variation within VP intervals.

With reference to FIG. 11, a technique for detecting PMT based on variations in VP intervals will now be described for use with a DDD system. Within FIG. 11, processing of the ventricular and atrial channels is not shown separately. Rather, the overall processing performed by the biventricular device is shown. Beginning at step 600, biventricular pacing is delivered to the heart of the patient. As pacing is delivered, the stimulation device measures and records the interval between V-pulses and subsequent P-waves (i.e. the VP interval), at step 602. More specifically, the VP interval is calculated to represent either the interval between LV pulses and P-waves or the interval between RV-pulses and P-waves. In a biventricular triggered system, the LV-pulse to P-wave interval is preferably employed. At step 604, the stimulation device evaluates the variation in VP intervals over a predetermined number of pacing cycles. The number of pacing cycles is preferably set to a value in the range of 2 to 32. Alternatively, VP variation is evaluated over a fixed period of time, preferably set to a value in the range of 2 to 32 seconds. In any case, at step 606, the device compares the amount of variation in the VP intervals with a predetermined threshold representative of the minimum amount of variation expected to be found within VP intervals. The threshold may be programmed by the physician using an external device or may be preprogrammed within the implantable device.

So long as the amount of variation in VP intervals exceeds the threshold, processing merely returns to step 600 for additional biventricular pacing. If, however, the amount of variation in VP intervals falls below the threshold, then the P-waves being detected are probably actually far field T-waves. In that case, to verify that T-wave oversensing is indeed occurring, the device determines the periodicity of P-waves on the atrial channel and calculates when the next suspect P-wave is expected. At step 608, the device delivers a pacing pulse to the atria at a point in time selected such that the atria should then be refractory during the next suspect P-wave. In one specific example, the pacing pulse is delivered to the atria approximately 300 to 330 milliseconds following the last detected P-wave. If the last detected P-wave was a true P-wave, then after about 300 milliseconds, the atria will again be receptive to a pacing pulse and the pacing pulse will be captured and the atria will again be refractory when the next expected P-wave would occur (as determined based on the periodicity of the P-waves). Hence, if another P-wave is indeed detected at the expected time that P-wave cannot be a true P-wave and must instead be some other electrical event, probably a far field T-wave. Accordingly, at step 610, the implantable device searches for a P-wave during a period of time in which the atria should be naturally refractory following the atrial pulse. The duration of this natural refractory period (which differs from the artificially applied PVARP) may be pre-programmed. If a P-wave is detected during the natural refractory period, then, at step 612, the device concludes that the periodic P-waves are actually far field T-waves (or other far field electrical events) and that PMT has begun. At step 614, the device automatically expands the PVARP on the atrial channel in an attempt to block the far field T-waves thereby breaking or terminating the PMT.

As noted above, far field T-waves on the atrial channel can be misinterpreted as sinus P-waves, thus triggering delivery of V-pulses on the ventricle channels a fixed period of time later. Hence, each V-pulse triggers a T-wave, which is misinterpreted as a sinus P-wave, which, in turn, triggers yet another V-pulse in a continuous loop. With this type of PMT, the interval between each V-pulse and the detected P-wave will therefore always be a fixed period of time (i.e. the pre-programmed time delay between P-wave and V-pulse.) Hence, there will be almost no variation within the detected VP interval. On the other hand, if PMT is not occurring, then there will be some reasonable amount of variation in VP interval, because of normal variations in the heart rate of the patient. In this manner, the amount of variation within the VP interval is used to detect PMT. By immediately expanding the PVARP on atrial channel, the far field T-wave will more likely fall within the PVARP and not be detected, thus terminating the PMT.

The evaluation of the amount of variation in the VP interval may be performed in accordance with otherwise conventional types of statistical analysis. In one example, the first standard deviation from the average VP interval is calculated and that value is compared against a threshold representative of the expected minimum standard deviation in the VP intervals. A wide variety of other statistical techniques can be employed as well.

Figure 12:
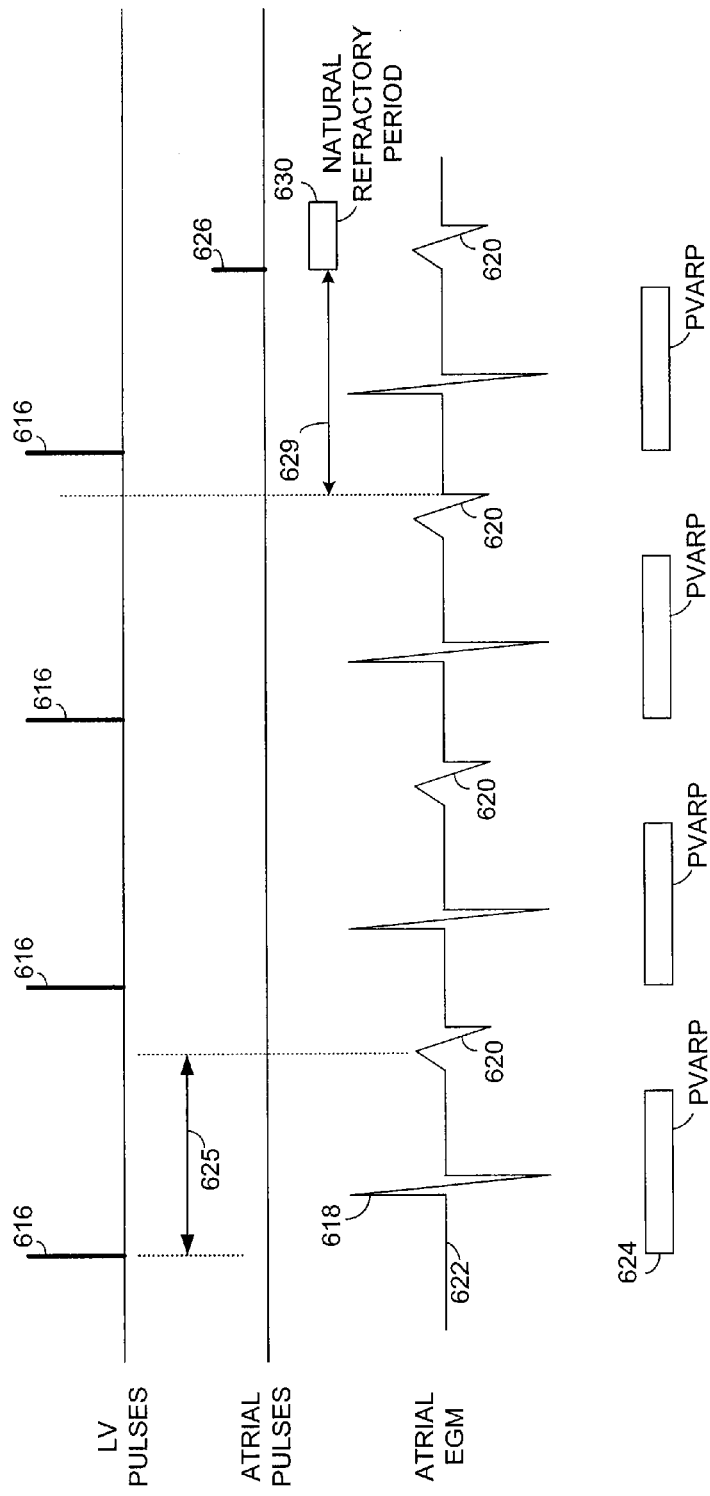
FIG. 12 is a graph further illustrating the technique of FIG. 11.

This technique is further illustrated in FIG. 12, which shows a sequence of LV pulses 616 delivered and resulting far field R-waves 618 and T-waves 620 sensed within an atrial IEGM 622. Also shown is a PVARP 624, which is not quite long enough to cover the T-wave. Hence, the implantable device detects the T-wave but misinterprets it as a P-wave. Since it is not a true P-wave, no R-wave occurs immediately thereafter and so the implantable device concludes that the ventricles failed to properly depolarize and that a V-pulse is thereby required. Hence, another V-pulse 616 is applied. This sequence repeats, resulting in a PMT exhibiting a fixed period between each V-pulse and the next detected P-wave, i.e. the VP interval 625. Therefore, the variation in the VP interval falls below the aforementioned threshold indicating that PMT may be occurring. To verify that PMT is indeed occurring, the implantable device delivers an A-pulse 626 to the atria a fixed period of time 629 following the latest detected P-wave, i.e. at a point in time when the atria should again be receptive to stimulus. If the last detected P-wave was indeed a true P-wave, then the A-pulse should be captured and no further P-waves should then be detectable during a natural refractory period 630 following the captured A-pulse. However, because the last detected P-wave was actually a T-wave that had been misinterpreted as a P-wave, then another T-wave 620 appears within the natural refractory period, thus verifying that PMT is ongoing. The PVARP can then be lengthened to cover the T-wave to break the PMT.

In one example, the PVARP is expanded by a predetermined amount set to be long enough to ensure that the T-wave will definitely be covered. Then, to optimize the PVARP length, the duration of the PVARP is incrementally decreased until the amount of variation in the VP interval again falls below the threshold. At that point, the PVARP is again incremented slightly, thus ensuring the PVARP will be just long enough in duration to cover far field T-waves without being unnecessarily long. Then an additional safety interval may be added to the PVARP. Periodically, perhaps once every hour, the duration of the PVARP is incrementally decreased until the amount of variation in the VP intervals begins to drop, then the PVARP is again incremented. In this manner, the PVARP is maintained at an optimal duration, i.e. the minimal duration necessary to safely prevent detection of far field T-waves on the atrial channel. The PVARP is not set to some arbitrarily long duration, regardless of the true VP intervals, since such an arbitrarily long PVARP duration could result in true sinus waves in being blanked as well.

2. Ventricular Interval-Based PMT Prevention

Figure 13:
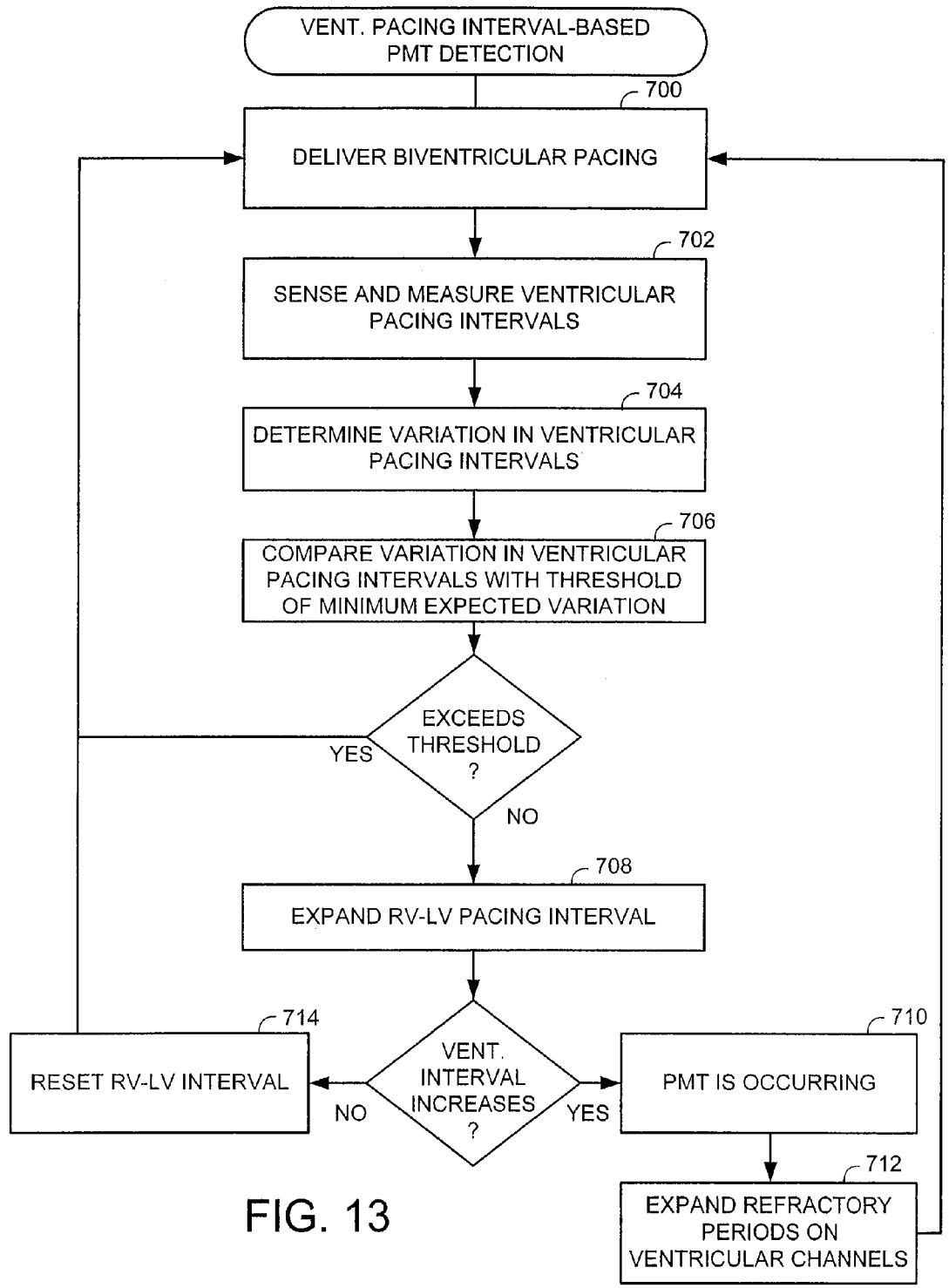
FIG. 13 is a flow chart providing an overview of the operation of a fourth exemplary embodiment of the invention and particularly illustrating the manner by which the PMT detection unit of the implantable stimulation device of FIGS. 1 and 2 operates to detect PMT based on a degree of variation detected within ventricular pacing intervals.
Figure 14:
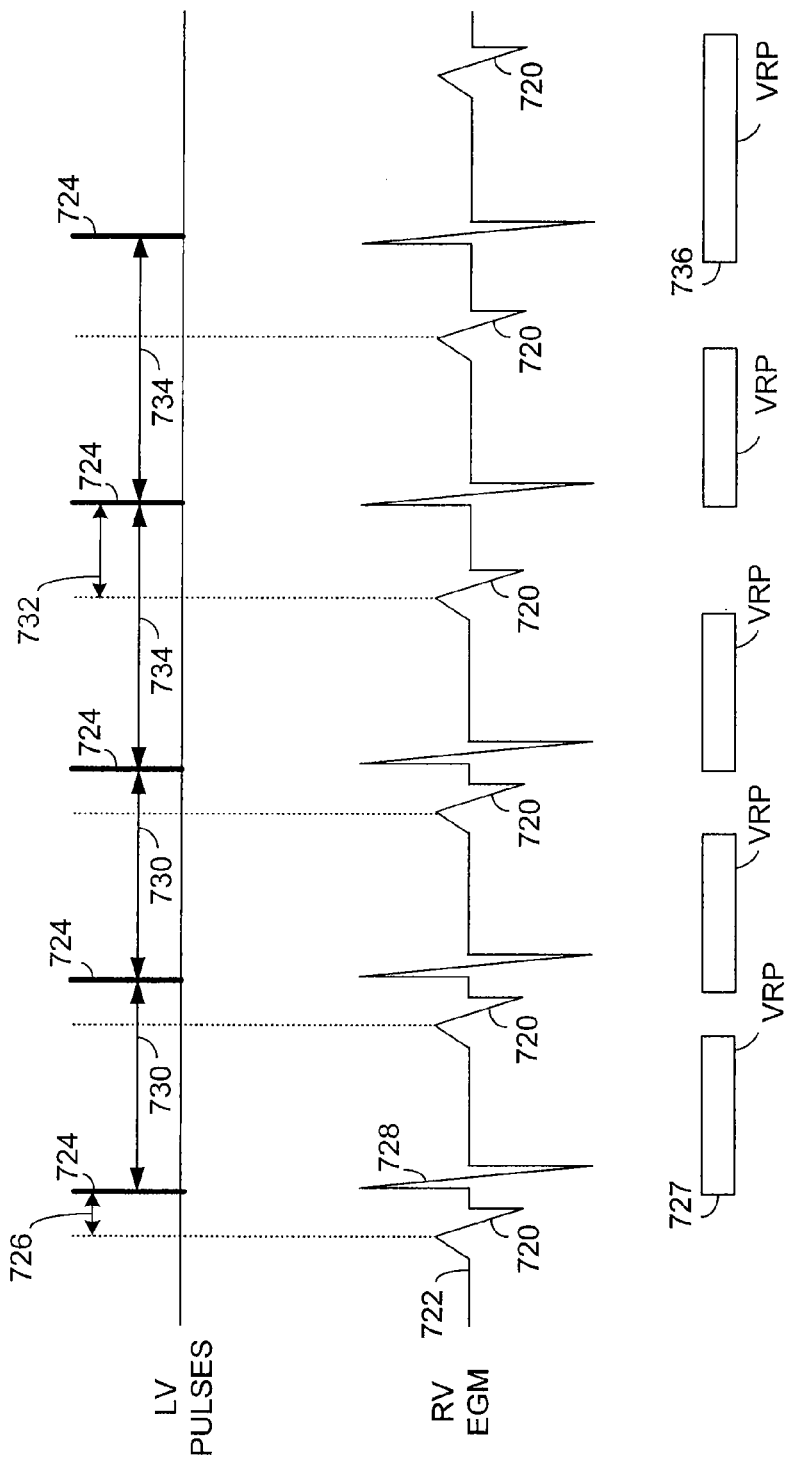
FIG. 14 is a graph further illustrating the technique of FIG. 13.

Referring now to FIGS. 13 and 14, a PMT detection technique is provided for use with biventricular triggered systems, which analyzes variations in ventricular pacing intervals. Beginning at step 700, the device begins delivering biventricular pacing. At step 702, the implantable device senses and measures ventricular pacing intervals, e.g. the intervals between consecutive LV-pulses. Note that this not the interval between the right and left pulses of a single pair of biventricular pulses (i.e. the RV-LV interval), which is a much smaller interval, e.g. 20 ms. At step 704, the implantable device determines the amount of variation in the ventricular pacing intervals, using statistical techniques similar to those described in connection with FIG. 11. At step 706, the implantable device compares the amount of variation with a threshold representative of the minimum amount of variation expected within the ventricular pacing intervals. This threshold may differ from the corresponding threshold described in connection with FIG. 11. The ventricular pacing variation threshold may vary as a function of time, e.g. dependent upon the current intrinsic ventricular rate. In any case, so long as the amount of variation in the ventricular pacing intervals exceeds the threshold, processing merely returns to step 700 for additional biventricular pacing. However, if the amount of variation falls below the threshold, then PMT may be occurring because of T-waves being misinterpreted as R-waves on the right ventricular channel. To verify that PMT is occurring, the implantable device expands the RV-LV pacing interval by at step 708 to, for example, 50 ms and determines whether the ventricular pacing interval increases by the same amount. If PMT is occurring because of T-wave oversensing the right ventricular channel, the ventricular pacing interval will increase by the same amount, and PMT is thereby detected at step 710. To break the PMT, refractory periods defined on the ventricular channels are expanded at step 710. If the ventricular pacing interval does not increase following step 708 by an equal amount, then the RV-LV interval is merely reset and biventricular pacing continues at step 700.

The technique of FIG. 13 is illustrated in FIG. 14 which shows T-waves 720 detected on a right ventricular EGM 722. The first T-wave is misinterpreted as an R-wave, triggering a LV pulse 724 following an RV-LV delay (identified by arrow 726). A ventricular refractory period (VRP) 727 is applied to the RV channel immediately upon delivery of the LV pulse.

The V-pulse causes a depolarization of the ventricles resulting in an R-wave 728, which is not detected. The VRP is not long enough to cover the next T-wave, which is again misinterpreted as an R-wave and so another V-pulse is delivered. The ventricular pacing interval between the consecutive V-pulses is identified by arrow 730. As can be seen, this interval is repeated until the RV-LV interval is increased (at step 708 of FIG. 13). The new RV-LV interval length is identified by arrow 732. The increase in RV-LV interval results in a corresponding increase in the ventricular pacing interval, as identified by arrow 734. Since the ventricular pacing interval increased by the same amount as the RV-LV interval increased, the implantable device thereby concludes PMT is occurring (at step 710 of FIG. 13) and increases the VRP to cover the T-wave. The longer VRP is identified by 736. The next T-wave is thereby covered by the VRP and is not detected nor misinterpreted as an R-wave and so PMT cycle is broken. As with the technique of FIG. 11, the expansion of the refractory period may be adaptive, i.e. the refractory period may be incrementally increased until the variation within the ventricular pacing interval exceeds the threshold, so as to achieve the minimum duration refractory period sufficient to cover the far field T-wave. Periodically, the duration of the refractory period is incrementally decreased to reset in the refractory period to a shorter duration, when permitted.

What have been described are various exemplary techniques for preventing the onset of PMT during biventricular pacing and for detecting and terminating PMT if it nevertheless occurs. Although described primarily with respect to an exemplary device capable of sensing and pacing at only a single location in each ventricle, principles of the invention are applicable to other pacing systems such as multi-site biventricular pacing devices capable of pacing at multiple sites within the right ventricle or within the left ventricle.

Thus FIGS. 13 and 14 illustrate a ventricular interval based PMT detection system for use within a triggered biventricular system. This embodiment is particularly suitable for use within modes wherein there is no atrial sensing because either there is no atrial lead or the patient is in atrial fibrillation and so the implantable device has mode-switched to a non-atrial tracking mode.

The embodiments described herein are merely illustrative of the invention and should not be construed as limiting the scope of the invention, which is to be interpreted in accordance with the claims that follow.

What is claimed is:

1. In an implantable cardiac stimulation device having a biventricular pacing system and a pacemaker mediated tachycardia (PMT) prevention system, a method comprising:
   delivering a pair of biventricular pacing pulses to left and right ventricles of a heart using the biventricular pacing system, the pair of biventricular pacing pulses comprising a first ventricular pacing pulse and a second ventricular pacing pulse; and
   triggering a post ventricular atrial refractory period (PVARP) upon delivery of the second ventricular pacing pulse to prevent onset of PMT.

2. The method of claim 1 wherein triggering a PVARP upon delivery of the second ventricular pacing pulse comprises:
   suspending sensing on an atrial sensing channel for a duration of the PVARP; and
   after the duration of the PVARP has expired, resuming processing of the atrial sensing channel.

3. The method of claim 1 wherein a duration of the PVARP comprises:
   deactivating atrial sense amplifiers during an atrial blanking period; and
   activating the atrial sense amplifiers to sense events on the atrial sensing channel during an atrial refractory period, the implantable cardiac stimulation device not responding to sensed events on the atrial sensing channel during the atrial refractory period.

4. The method of claim 1 wherein a duration of the PVARP more effectively covers both a far field T-wave associated with the first ventricular pacing pulse and a far field T-wave associated with the second ventricular pacing pulse on an atrial sensing channel by triggering the PVARP upon delivery of the second ventricular pacing pulse, and wherein the PVARP may expire by the time the T-wave associated with the second ventricular pacing pulse is generated and propagated to atrial sensing locations if the PVARP is triggered upon delivery of the first ventricular pacing pulse.

5. The method of claim 1 wherein a duration of the PVARP comprises a standard duration to avoid improperly covering a subsequent true P-wave during high heart rates.

6. The method of claim 1 wherein delivering a pair of biventricular pacing pulses to the left and right ventricles of the heart comprises timing the delivery of the first ventricular pacing pulse and the second ventricular pacing pulse to optimally synchronize contraction between the left and right ventricles.

7. In an implantable cardiac stimulation device having a biventricular pacing system and a pacemaker mediated tachycardia (PMT) detection and termination system, a method comprising:
   determining a sequence for delivery of a pair of biventricular pacing pulses to a first ventricle and a second ventricle using the biventricular pacing system, the pair of biventricular pacing pulses comprising a first ventricular pacing pulse to the first ventricle and a second ventricular pacing pulse to the second ventricle;
   delivering the first ventricular pacing pulse to the first ventricle in accordance with the sequence determined by the biventricular pacing system;
   delivering the second ventricular pacing pulse to the second ventricle in accordance with the sequence determined by the biventricular pacing system; and
   triggering a post ventricular atrial refractory period (PVARP) upon delivery of the second ventricular pacing pulse using the PMT detection and termination system to prevent onset of PMT.

8. The method of claim 7 wherein triggering a PVARP upon delivery of the second ventricular pacing pulse comprises:
   suspending sensing on an atrial sensing channel for a duration of the PVARP; and
   after the duration of the PVARP has expired, resuming processing of the atrial sensing channel.

9. The method of claim 7 wherein a duration of the PVARP comprises:
   deactivating atrial sense amplifiers during an atrial blanking period; and
   activating the atrial sense amplifiers for sensing events on an atrial sensing channel during an atrial refractory period, the implantable cardiac stimulation device not responding to sensed events on the atrial sensing channel during the atrial refractory period.

10. The method of claim 7 wherein a duration of the PVARP more effectively covers both a far field T-wave associated with the first ventricular pacing pulse and a far field T-wave associated with the second ventricular pacing pulse by triggering the PVARP upon delivery of the second ventricular pacing pulse, and wherein the PVARP may expire by the time the T-wave associated with the second ventricular pacing pulse is generated and propagated to atrial sensing locations if the PVARP is triggered upon delivery of the first ventricular pacing pulse.

11. The method of claim 7 wherein a duration of the PVARP comprises a standard duration to avoid improperly covering a subsequent true P-wave during high heart rates.

12. The method of claim 7 wherein delivering a pair of biventricular pacing pulses to the left and right ventricles of the heart comprises timing the delivery of the first ventricular pacing pulse and the second ventricular pacing pulse to optimally synchronize contraction between the left and right ventricles.

13. An implantable cardiac stimulation device comprising:
a pulse generator delivering a pair of biventricular pacing pulses to left and right ventricles of a heart, the pair of biventricular pacing pulses comprising a first ventricular pacing pulse and a second ventricular pacing pulse;
an atrial sensing channel sensing atrial activity;
a controller that is operative to control the pulse generator to deliver the pair of biventricular pacing pulses; and
a pacemaker mediated tachycardia (PMT) prevention system to trigger a post ventricular atrial refractory period (PVARP) upon delivery of the second ventricular pacing pulse to prevent onset of PMT.

14. The device of claim 13 wherein the PMT prevention system suspends sensing on the atrial sensing channel for a duration of the PVARP and resumes processing of the atrial sensing channel after the duration of the PVARP has expired.

15. The device of claim 13 wherein a duration of the PVARP comprises:
an atrial blanking period during which atrial sense amplifiers are deactivated; and
an atrial refractory period during which the atrial sense amplifiers are active for sensing events on the atrial sense channel and during which the cardiac stimulation device is not responsive to sensed events on the atrial sensing channel.

16. The device of claim 13 wherein a duration of the PVARP more effectively covers both a far field T-wave associated with the first ventricular pacing pulse and a far field T-wave associated with the second ventricular pacing pulse by triggering the PVARP upon delivery of the second ventricular pacing pulse, and wherein the PVARP may expire by the time the T-wave associated with the second ventricular pacing pulse is generated and propagated to atrial sensing locations if the PVARP is triggered upon delivery of the first ventricular pacing pulse.

17. The device of claim 13 wherein a duration of the PVARP comprises a standard duration to avoid improperly covering a subsequent true P-wave during high heart rates.

18. The device of claim 13 wherein the pulse generator delivering a pair of biventricular pacing pulses to the left and right ventricles of the heart comprises timing the delivery of the first ventricular pacing pulse and the second ventricular pacing pulse to optimally synchronize contraction between the left and right ventricles.

19. An implantable cardiac stimulation device comprising:
a biventricular pacing system determining a sequence for delivery of a pair of pacing pulses to a first ventricle and a second ventricle, the pair of biventricular pacing pulses comprising a first ventricular pacing pulse to the first ventricle and a second ventricular pacing pulse to the second ventricle; and
a pacemaker mediated tachycardia (PMT) detection and termination system triggering a post ventricular atrial refractory period (PVARP) upon delivery of the second ventricular pacing pulse to prevent onset of PMT.

20. The device of claim 19 wherein the PMT detection and termination system suspends sensing on the atrial sensing channel for a duration of the PVARP and resumes processing of the atrial sensing channel after the duration of the PVARP has expired.

21. The device of claim 19 wherein a duration of the PVARP comprises:
an atrial blanking period during which atrial sense amplifiers are deactivated; and
an atrial refractory period during which the atrial sense amplifiers are active for sensing events on the atrial sensing channel and during which the cardiac stimulation device is not responsive to sensed events on the atrial sensing channel.

22. The device of claim 19 wherein a duration of the PVARP more effectively covers both a far field T-wave associated with the first ventricular pacing pulse and a far field T-wave associated with the second ventricular pacing pulse on an atrial sensing channel by triggering the PVARP upon delivery of the second ventricular pacing pulse, and wherein the PVARP may expire by the time the T-wave associated with the second ventricular pacing pulse is generated and propagated to atrial sensing locations if the PVARP is triggered upon delivery of the first ventricular pacing pulse.

23. The device of claim 19 wherein a duration of the PVARP comprises a standard duration to avoid improperly covering a subsequent true P-wave during high heart rates.

24. The device of claim 19 wherein the biventricular pacing system times the delivery of the first ventricular pacing pulse and the second ventricular pacing pulse to optimally synchronize contraction between the left and right ventricles.

* * * * *